United States Patent
Suh et al.

(10) Patent No.: US 10,977,349 B2
(45) Date of Patent: Apr. 13, 2021

(54) ELECTRONIC DEVICE FOR AUTHENTICATING BIOMETRIC DATA AND SYSTEM

(71) Applicant: Samsung Electronics Co., Ltd, Suwon-si (KR)

(72) Inventors: Kanghyun Suh, Seoul (KR); Doosuk Kang, Suwon-si (KR); Bokun Choi, Seoul (KR); Jeongmin Park, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 519 days.

(21) Appl. No.: 15/886,620

(22) Filed: Feb. 1, 2018

(65) Prior Publication Data

US 2018/0225437 A1 Aug. 9, 2018

(30) Foreign Application Priority Data

Feb. 3, 2017 (KR) ........................ 10-2017-0015437

(51) Int. Cl.
*G06F 21/00* (2013.01)
*G06F 21/32* (2013.01)
(Continued)

(52) U.S. Cl.
CPC ............ *G06F 21/32* (2013.01); *A61B 5/0261* (2013.01); *A61B 5/04* (2013.01); *A61B 5/0402* (2013.01);
(Continued)

(58) Field of Classification Search
None
See application file for complete search history.

(56) References Cited

U.S. PATENT DOCUMENTS

| 6,845,263 | B2 * | 1/2005 | Kawaguchi .......... A61B 5/0285 600/504 |
| 2002/0013717 | A1 * | 1/2002 | Ando ....................... A61B 5/22 705/4 |

(Continued)

FOREIGN PATENT DOCUMENTS

| KR | 10-2016-0029264 A | 3/2016 |
| KR | 10-2016-0083032 A | 7/2016 |

(Continued)

OTHER PUBLICATIONS

Communication from a foreign patent office in a counterpart foreign application, European Patent Office, "European Search Report," Application No. EP 18154873.6, dated Jun. 7, 2018, 6 pages.

(Continued)

*Primary Examiner* — Maung T Lwin

(57) ABSTRACT

The present disclosure provides an electronic device and system that include an electrode interface that can be brought in contact with the body of a user, a memory, and a processor operably coupled to the electrode interface and the memory, in which the processor is set to obtain user information through user authentication, generate a user authentication signal on the basis of the user information, and transmit the user authentication signal or a signal including at least a portion of the user authentication signal through the body of a user being in contact with the electrode interface.

20 Claims, 12 Drawing Sheets

(51) Int. Cl.
    H04L 9/32      (2006.01)
    H04L 29/06     (2006.01)
    A61B 5/026     (2006.01)
    A61B 5/00      (2006.01)
    A61B 5/0402    (2006.01)
    A61B 5/117     (2016.01)
    G06K 9/00      (2006.01)
    H04W 12/06     (2021.01)
    A61B 5/04      (2006.01)
    A61B 5/0533    (2021.01)
    A61B 5/053     (2021.01)
    H04W 88/02     (2009.01)

(52) U.S. Cl.
    CPC .............. *A61B 5/117* (2013.01); *A61B 5/681*
        (2013.01); *A61B 5/6824* (2013.01); *A61B
        5/6832* (2013.01); *G06K 9/00885* (2013.01);
        *H04L 9/3231* (2013.01); *H04L 63/0861*
        (2013.01); *H04W 12/0605* (2019.01); *H04W
        12/0608* (2019.01); *A61B 5/053* (2013.01);
        *A61B 5/0533* (2013.01); *A61B 5/4809*
        (2013.01); *A61B 2560/0204* (2013.01); *A61B
        2560/0242* (2013.01); *A61B 2562/0219*
        (2013.01); *A61B 2562/0257* (2013.01); *G06K
        2009/00939* (2013.01); *H04W 88/02* (2013.01)

(56) References Cited

U.S. PATENT DOCUMENTS

| | | | | |
|---|---|---|---|---|
| 2005/0280531 | A1* | 12/2005 | Fadem | A61B 5/0428 340/539.12 |
| 2007/0280515 | A1* | 12/2007 | Goto | G06F 21/32 382/124 |
| 2010/0060586 | A1* | 3/2010 | Pisula | G06F 3/04886 345/169 |
| 2010/0138914 | A1* | 6/2010 | Davis | H04L 9/3231 726/19 |
| 2011/0257546 | A1* | 10/2011 | Gozzini | A61B 5/0404 600/509 |
| 2013/0321168 | A1* | 12/2013 | Mahony | A61B 5/002 340/870.09 |
| 2014/0009262 | A1 | 1/2014 | Robertson et al. | |
| 2015/0146944 | A1* | 5/2015 | Pi | G06F 21/83 382/124 |
| 2015/0161461 | A1 | 6/2015 | McNulty et al. | |
| 2016/0154952 | A1* | 6/2016 | Venkatraman | G06Q 20/3278 705/44 |
| 2016/0342782 | A1* | 11/2016 | Mullins | G06F 21/32 |
| 2017/0007183 | A1 | 1/2017 | Dusan et al. | |
| 2017/0038848 | A1* | 2/2017 | Yuen | G01S 19/00 |
| 2017/0071469 | A1* | 3/2017 | Hijazi | A61B 5/04085 |
| 2017/0136265 | A1* | 5/2017 | Hyde | A61B 5/45 |
| 2017/0319082 | A1* | 11/2017 | Sayme | A61B 5/04017 |

FOREIGN PATENT DOCUMENTS

| | | |
|---|---|---|
| KR | 10-2016-0108491 A | 9/2016 |
| KR | 10-2016-0118164 A | 10/2016 |

OTHER PUBLICATIONS

Cherukuri, Sriram, et al., "BioSec: A Biometric Based Approach for Securing Communication in Wireless Networks of Biosensors Implanted in the Human Body," IEEE Computer Society, Proceedings of the 2003 International Conference on Parallel Processing Workshops (ICPPW'03), 2003 IEEE, 8 pages.

Wang, Honggang, et al., "An Integrated Biometric-based Security Framework Using Wavelet-Domain HMM in Wireless Body Area Networks (WBAN)," IEEE Communications Society, IEEE, 2011, 5 pages.

* cited by examiner

ELECTRONIC DEVICE FOR AUTHENTICATING BIOMETRIC DATA AND SYSTEM

CROSS-REFERENCE TO RELATED APPLICATION

This application is related to and claims priority under 35 U.S.C. § 119(a) to Korean Patent Application No. 10-2017-0015437 filed on Feb. 3, 2017, the entire content of which is hereby incorporated by reference.

TECHNICAL FIELD

The present disclosure relates to an electronic device and system for authenticating biometric data.

BACKGROUND

Recently, various electronic devices such as a mobile communication terminal, a PDA (Personal Digital Assistant), an electronic notebook, a smartphone, a tablet PC (Personal Computer), and a wearable device have been popularized with the development of digital technology. Such electronic devices have been developed in terms of hardware and/or software to support and improve functions. For example, electronic devices are equipped with a fingerprint sensor, an iris sensor, or a biometric sensor.

Meanwhile, as interest in health has increased, an interest in exercise has also increased. To follow this trend, electronic devices are provided with various services for obtaining and monitoring users' biometric information and exercise information, using biometric sensors.

SUMMARY

Although there is biometric information obtained by a biometric sensor or an electronic device including a biometric sensor, it may be very difficult to know whom the biometric information actually belongs to on the basis of the biometric information itself. That is, it may be difficult to know whether biometric information has been actually measured from a specific user or from other users.

An electronic device according to various embodiments includes an electrode interface that can be brought in contact with the body of a user, a memory, and a processor operably coupled to the electrode interface and the memory. The processor may be set to obtain user information through user authentication, generate a user authentication signal on the basis of the user information, and transmit the user authentication signal or a signal including at least a portion of the user authentication signal through the body of the user being in contact with the electrode interface.

An electronic device that is brought in contact with a body according to various embodiments may include an electrode interface that can be brought in contact with the body of a user, a memory, and a processor operably coupled to the electrode interface and the memory. The processor may be set to obtain biometric information using the electrode interface, to receive a user authentication signal or a signal including at least a portion of the user authentication signal from the electrode interface, and to store the at least one item of biometric information in the memory together with the user authentication signal.

A system including a first electronic device and a second electronic device according to various embodiments includes: as the first electronic device, a first electrode interface that can be brought in contact with the body of a user and a first processor operably coupled to the first electrode interface, wherein the first processor generates a user authentication signal on the basis of user information obtained through user authentication and transmits the user authentication signal or a signal including at least a portion of the user authentication signal through the body of a user being in contact with the first electrode interface; and as the second electronic device, a second electrode interface that can be brought in contact with the body of a user, a memory, and a second processor operably coupled to the second electrode interface and the memory, wherein the second processor can obtain at least one item of biometric information using the second electrode interface, receive a user authentication signal or a signal including at least a portion of the user authentication signal from the second electrode interface, and store the at least one item of biometric information in the memory together with the user authentication signal.

According to various embodiments, when biometric information of a user is measured, biometric information measured by applying a user authentication signal or a portion of the user authentication signal to the body of the user and the user authentication signal are stored together, whereby it is possible to prove that the biometric information was measured from the user.

According to various embodiments, a first electronic device can transmit a user authentication signal to a second electronic device through the body of a user without paring the first electronic device that generates the user authentication signal and the second electronic device that obtains biometric information of the user.

According to various embodiments, power consumption by separate electronic devices can be minimized and the first electronic device can transmit a user authentication signal or a portion of the user authentication signal to the second electronic device through the body of a user.

According to various embodiments, it is possible to manufacture the second electronic device that obtains biometric information of a user at a low cost.

According to various embodiments, it is possible to prove that biometric information measured using a user authentication signal including user information or a portion of the user authentication signal was measured from a user.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
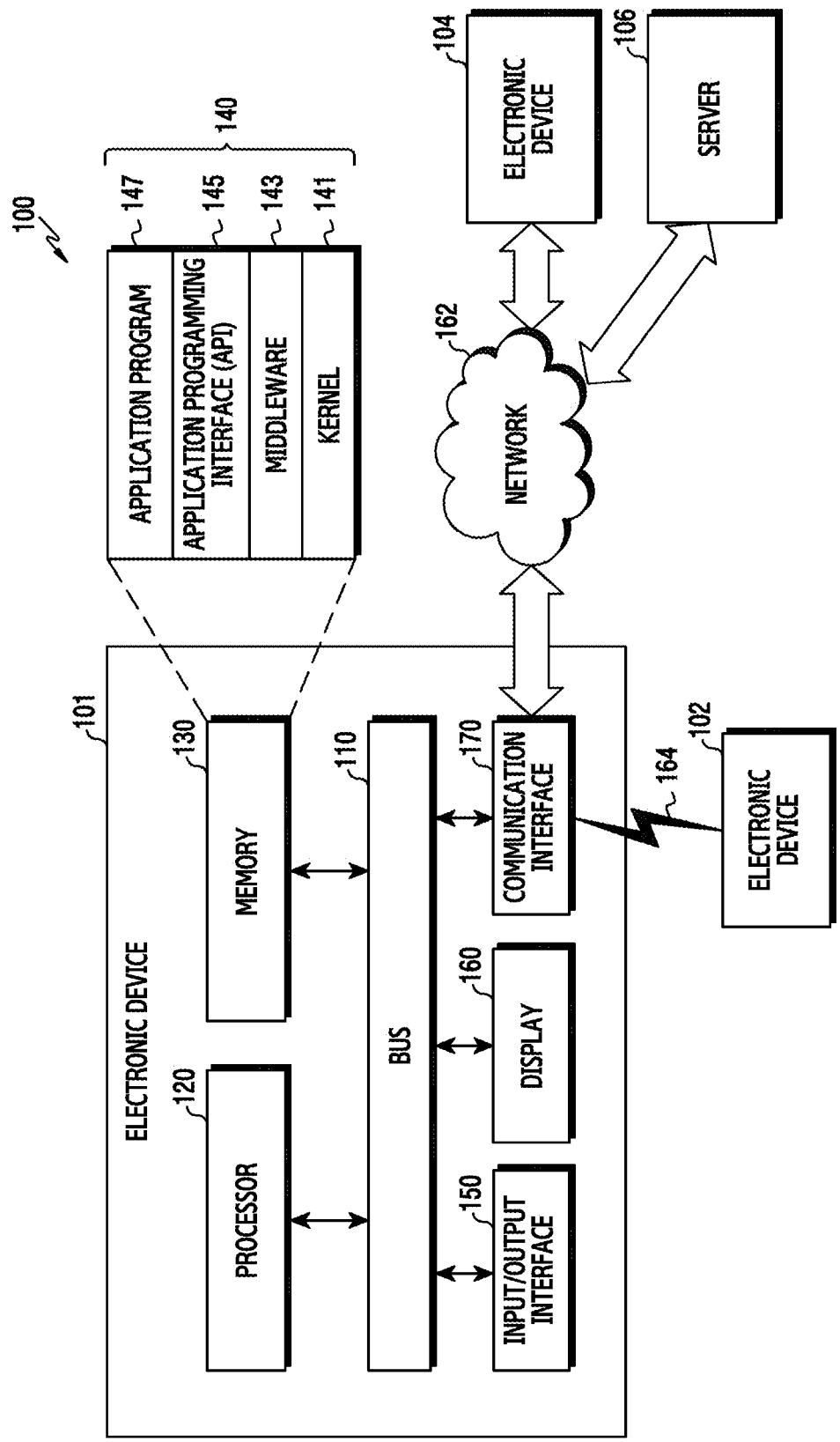
FIG. 1 illustrates a diagram of an electronic device in a network environment according to various embodiments.

FIGS. 1 through 12, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

As used herein, the expression "have", "may have", "include", or "may include" refers to the existence of a corresponding feature (e.g., numeral, function, operation, or constituent element such as component), and does not exclude one or more additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), the element may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) for performing the corresponding operations or a generic-purpose processor (e.g., central processing unit (CPU) or application processor (AP)) that can perform the corresponding operations by executing one or more software programs stored in a memory device.

The terms used in the present disclosure are only used to describe specific embodiments, and are not intended to limit the present disclosure. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

An electronic device according to various embodiments of the present disclosure may include at least one of, for example, a smart phone, a tablet Personal Computer (PC), a mobile phone, a video phone, an electronic book reader (e-book reader), a desktop PC, a laptop PC, a netbook computer, a workstation, a server, a Personal Digital Assistant (PDA), a Portable Multimedia Player (PMP), a MPEG-1 audio layer-3 (MP3) player, a mobile medical device, a camera, and a wearable device. According to various embodiments, the wearable device may include at least one of an accessory type (e.g., a watch, a ring, a bracelet, an anklet, a necklace, a glasses, a contact lens, or a Head-Mounted Device (HMD)), a fabric or clothing integrated type (e.g., an electronic clothing), a body-mounted type (e.g., a skin pad, or tattoo), and a bio-implantable type (e.g., an implantable circuit).

According to some embodiments, the electronic device may be a home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync®, Apple TV®, or Google TV®), a game console (e.g., Xbox® and PlayStation®), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). The electronic device according to various embodiments of the present disclosure may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology.

Hereinafter, an electronic device according to various embodiments will be described with reference to the accompanying drawings. As used herein, the term "user" may indicate a person who uses an electronic device or a device (e.g., an artificial intelligence electronic device) that uses an electronic device.

FIG. 1 illustrates a network environment including an electronic device according to various embodiments of the present disclosure.

An electronic device 101 within a network environment, according to various embodiments, will be described with reference to FIG. 1. The electronic device 101 may include a bus 110, a processor 120, a memory 130, an input/output interface 150, a display 160, and a communication interface 170. According to an embodiment of the present disclosure, the electronic device 101 may omit at least one of the above components or may further include other components.

The bus 110 may include, for example, a circuit which interconnects the components 110 to 170 and delivers a communication (e.g., a control message and/or data) between the components 110 to 170.

The processor 120 may include one or more of a Central Processing Unit (CPU), an Application Processor (AP), and a Communication Processor (CP). The processor 120 may carry out, for example, calculation or data processing relating to control and/or communication of at least one other component of the electronic device 101.

The memory 130 may include a volatile memory and/or a non-volatile memory. The memory 130 may store, for example, commands or data relevant to at least one other component of the electronic device 101. According to an embodiment of the present disclosure, the memory 130 may store software and/or a program 140. The program 140 may include, for example, a kernel 141, middleware 143, an Application Programming Interface (API) 145, and/or application programs (or "applications") 147. At least some of the kernel 141, the middleware 143, and the API 145 may be referred to as an Operating System (OS).

The kernel 141 may control or manage system resources (e.g., the bus 110, the processor 120, or the memory 130) used for performing an operation or function implemented in the other programs (e.g., the middleware 143, the API 145, or the application programs 147). Furthermore, the kernel 141 may provide an interface through which the middleware 143, the API 145, or the application programs 147 may access the individual components of the electronic device 101 to control or manage the system resources.

The middleware 143, for example, may serve as an intermediary for allowing the API 145 or the application programs 147 to communicate with the kernel 141 to exchange data.

Also, the middleware 143 may process one or more task requests received from the application programs 147 according to priorities thereof. For example, the middleware 143 may assign priorities for using the system resources (e.g., the bus 110, the processor 120, the memory 130, or the like) of the electronic device 101, to at least one of the application programs 147. For example, the middleware 143 may perform scheduling or loading balancing on the one or more task requests by processing the one or more task requests according to the priorities assigned thereto.

The API 145 is an interface through which the applications 147 control functions provided from the kernel 141 or the middleware 143, and may include, for example, at least one interface or function (e.g., instruction) for file control, window control, image processing, character control, and the like.

The input/output interface 150, for example, may function as an interface that may transfer commands or data input from a user or another external device to the other element(s) of the electronic device 101. Furthermore, the input/output interface 150 may output the commands or data received from the other element(s) of the electronic device 101 to the user or another external device.

Examples of the display 160 may include a Liquid Crystal Display (LCD), a Light-Emitting Diode (LED) display, an Organic Light-Emitting Diode (OLED) display, a Micro-ElectroMechanical Systems (MEMS) display, and an electronic paper display. The display 160 may display, for example, various types of contents (e.g., text, images, videos, icons, or symbols) to users. The display 160 may include a touch screen, and may receive, for example, a touch, gesture, proximity, or hovering input using an electronic pen or a user's body part.

The communication interface 170 may establish communication, for example, between the electronic device 101 and an external device (e.g., a first external electronic device 102, a second external electronic device 104, or a server 106). For example, the communication interface 170 may be connected to a network 162 through wireless or wired communication, and may communicate with an external device (e.g., the second external electronic device 104 or the server 106). The wireless communication may use at least one of, for example, Long Term Evolution (LTE), LTE-Advance (LTE-A), Code Division Multiple Access (CDMA), Wideband CDMA (WCDMA), Universal Mobile Telecommunications System (UMTS), Wireless Broadband (WiBro), and Global System for Mobile Communications (GSM), as a cellular communication protocol. In addition, the wireless communication may include, for example, short range communication 164. The short-range communication 164 may include at least one of, for example, Wi-Fi, Bluetooth, Near Field Communication (NFC), and Global Navigation Satellite System (GNSS). GNSS may include, for example, at least one of global positioning system (GPS), global navigation satellite system (Glonass), Beidou Navigation satellite system (Beidou) or Galileo, and the European global satellite-based navigation system, based on a location, a bandwidth, or the like. Hereinafter, in the present disclosure, the "GPS" may be interchangeably used with the "GNSS". The wired communication may include, for example, at least one of a Universal Serial Bus (USB), a High Definition Multimedia Interface (HDMI), Recommended Standard 232 (RS-232), and a Plain Old Telephone Service (POTS). The network 162 may include at least one of a telecommunication network such as a computer network (e.g., a LAN or a WAN), the Internet, and a telephone network.

Each of the first and second external electronic devices 102 and 104 may be of a type identical to or different from that of the electronic device 101. According to an embodiment of the present disclosure, the server 106 may include a group of one or more servers. According to various embodiments of the present disclosure, all or some of the operations performed in the electronic device 101 may be executed in another electronic device or a plurality of electronic devices (e.g., the electronic devices 102 and 104 or the server 106). According to an embodiment of the present disclosure, when the electronic device 101 has to perform some functions or services automatically or in response to a request, the electronic device 101 may request another device (e.g., the electronic device 102 or 104 or the server 106) to execute at least some functions relating thereto instead of or in addition to autonomously performing the functions or services. Another electronic device (e.g., the electronic device 102 or 104, or the server 106) may execute the requested functions or the additional functions, and may deliver a result of the execution to the electronic device 101. The electronic device 101 may process the received result as is or additionally, and may provide the requested functions or services. To this end, for example, cloud computing, distributed computing, or client-server computing technologies may be used.

Figure 2:
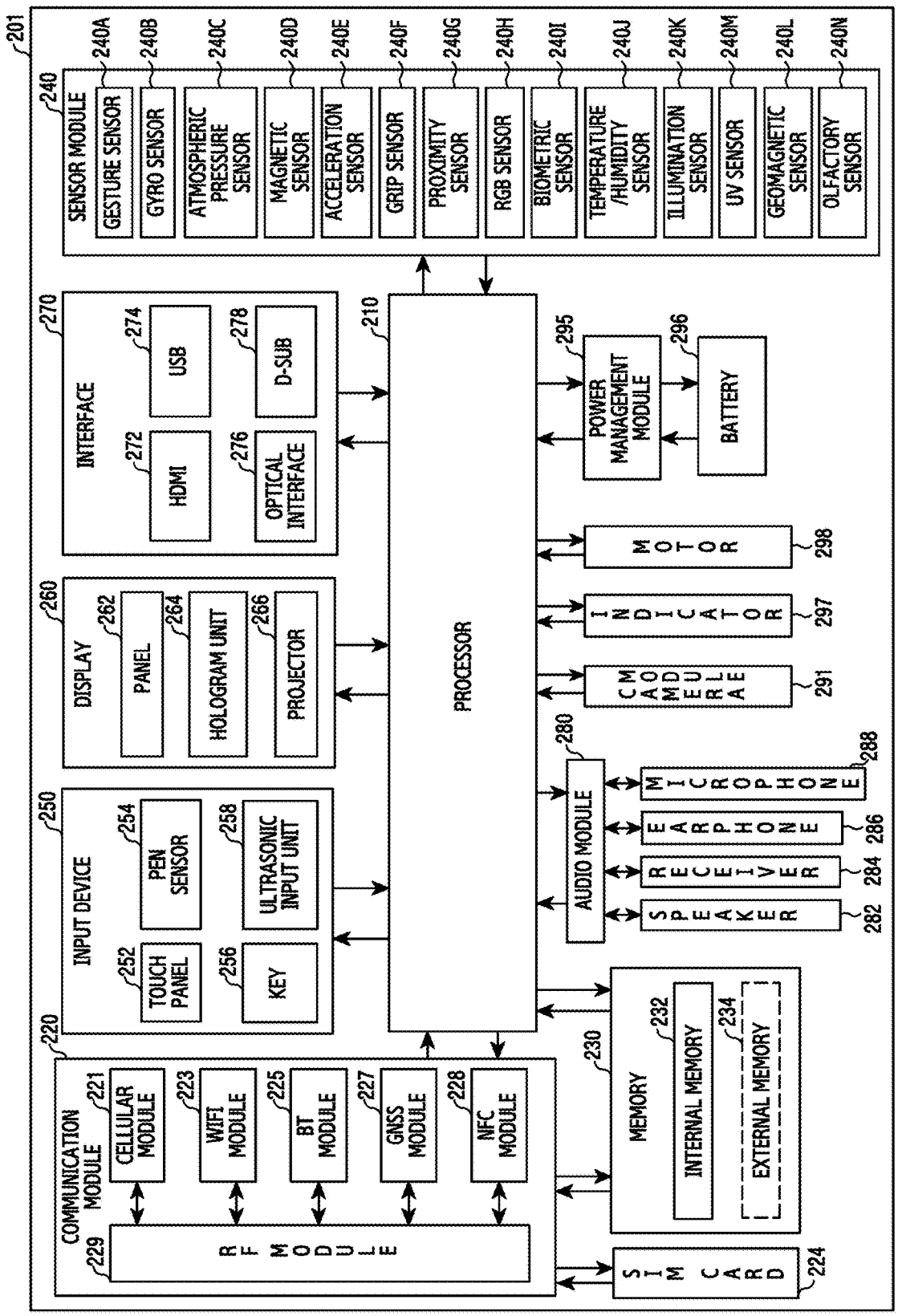
FIG. 2 illustrates a block diagram of the configuration of the electronic device according to various embodiments.

FIG. 2 illustrates a block diagram of an electronic device according to various embodiments of the present disclosure.

The electronic device 201 may include, for example, all or a part of the electronic device 101 shown in FIG. 1. The electronic device 201 may include one or more processors 210 (e.g., Application Processors (AP)), a communication module 220, a Subscriber Identification Module (SIM) 224, a memory 230, a sensor module 240, an input device 250, a display 260, an interface 270, an audio module 280, a camera module 291, a power management module 295, a battery 296, an indicator 297, and a motor 298.

The processor 210 may control a plurality of hardware or software components connected to the processor 210 by driving an operating system or an application program, and perform processing of various pieces of data and calculations. The processor 210 may be embodied as, for example, a System on Chip (SoC). According to an embodiment of the present disclosure, the processor 210 may further include a Graphic Processing Unit (GPU) and/or an image signal processor. The processor 210 may include at least some (for example, a cellular module 221) of the components illustrated in FIG. 2. The processor 210 may load, into a volatile memory, commands or data received from at least one (e.g., a non-volatile memory) of the other components and may process the loaded commands or data, and may store various data in a non-volatile memory.

The communication module 220 may have a configuration equal or similar to that of the communication interface 170 of FIG. 1. The communication module 220 may include, for example, a cellular module 221, a Wi-Fi module 223, a BT module 225, a GNSS module 227 (e.g., a GPS module 227, a Glonass module, a Beidou module, or a Galileo module), an NFC module 228, and a Radio Frequency (RF) module 229.

The cellular module 221, for example, may provide a voice call, a video call, a text message service, or an Internet service through a communication network. According to an embodiment of the present disclosure, the cellular module 221 may distinguish and authenticate the electronic device 201 in a communication network using the subscriber identification module 224 (for example, the SIM card). According to an embodiment of the present disclosure, the cellular module 221 may perform at least some of the functions that the AP 210 may provide. According to an embodiment of the present disclosure, the cellular module 221 may include a communication processor (CP).

For example, each of the Wi-Fi module 223, the BT module 225, the GNSS module 227, and the NFC module 228 may include a processor for processing data transmitted/received through a corresponding module. According to an embodiment of the present disclosure, at least some (e.g., two or more) of the cellular module 221, the Wi-Fi module 223, the BT module 225, the GNSS module 227, and the NFC module 228 may be included in one Integrated Chip (IC) or IC package.

The RF module 229, for example, may transmit/receive a communication signal (e.g., an RF signal). The RF module 229 may include, for example, a transceiver, a Power Amplifier Module (PAM), a frequency filter, a Low Noise Amplifier (LNA), and an antenna. According to another embodiment of the present disclosure, at least one of the cellular module 221, the WIFI module 223, the BT module 225, the GNSS module 227, and the NFC module 228 may transmit/receive an RF signal through a separate RF module.

The subscriber identification module 224 may include, for example, a card including a subscriber identity module and/or an embedded SIM, and may contain unique identification information (e.g., an Integrated Circuit Card Identifier (ICCID)) or subscriber information (e.g., an International Mobile Subscriber Identity (IMSI)).

The memory 230 (e.g., the memory 130) may include, for example, an embedded memory 232 or an external memory 234. The embedded memory 232 may include at least one of a volatile memory (e.g., a Dynamic Random Access Memory (DRAM), a Static RAM (SRAM), a Synchronous Dynamic RAM (SDRAM), and the like) and a non-volatile memory (e.g., a One Time Programmable Read Only Memory (OTPROM), a Programmable ROM (PROM), an Erasable and Programmable ROM (EPROM), an Electrically Erasable and Programmable ROM (EEPROM), a mask ROM, a flash ROM, a flash memory (e.g., a NAND flash memory or a NOR flash memory), a hard disc drive, a Solid State Drive (SSD), and the like).

The external memory 234 may further include a flash drive, for example, a Compact Flash (CF), a Secure Digital (SD), a Micro Secure Digital (Micro-SD), a Mini Secure Digital (Mini-SD), an eXtreme Digital (xD), a MultiMedia-Card (MMC), a memory stick, or the like. The external memory 234 may be functionally and/or physically connected to the electronic device 201 through various interfaces.

The sensor module 240, for example, may measure a physical quantity or detect an operation state of the electronic device 201, and may convert the measured or detected information into an electrical signal. The sensor module 240 may include, for example, at least one of a gesture sensor 240A, a gyro sensor 240B, an atmospheric pressure sensor (barometer) 240C, a magnetic sensor 240D, an acceleration sensor 240E, a grip sensor 240F, a proximity sensor 240G, a color sensor 240H (e.g., red, green, and blue (RGB) sensor), a biometric sensor (medical sensor) 240I, a temperature/humidity sensor 240J, an illuminance sensor 240K, and a Ultra Violet (UV) sensor 240M. Additionally or alternatively, the sensor module 240 may include, for example, an E-nose sensor, an electromyography (EMG) sensor, an electroencephalogram (EEG) sensor, an electrocardiogram (ECG) sensor, an Infrared (IR) sensor, an iris scan sensor, and/or a finger scan sensor. The sensor module 240 may further include a control circuit for controlling one or more sensors included therein. According to an embodiment of the present disclosure, the electronic device 201 may further include a processor configured to control the sensor module 240, as a part of the processor 210 or separately from the processor 210, and may control the sensor module 240 while the processor 210 is in a sleep state.

The input device 250 may include, for example, a touch panel 252, a (digital) pen sensor 254, a key 256, or an ultrasonic input device 258. The touch panel 252 may use, for example, at least one of a capacitive type, a resistive type, an infrared type, and an ultrasonic type. The touch panel 252 may further include a control circuit. The touch panel 252 may further include a tactile layer, and provide a tactile reaction to the user.

The (digital) pen sensor 254 may include, for example, a recognition sheet which is a part of the touch panel or is separated from the touch panel. The key 256 may include, for example, a physical button, an optical key or a keypad. The ultrasonic input device 258 may detect, through a microphone (e.g., the microphone 288), ultrasonic waves generated by an input tool, and identify data corresponding to the detected ultrasonic waves.

The display 260 (e.g., the display 160) may include a panel 262, a hologram device 264, or a projector 266. The panel 262 may include a configuration identical or similar to the display 160 illustrated in FIG. 1. The panel 262 may be implemented to be, for example, flexible, transparent, or wearable. The panel 262 may be embodied as a single module with the touch panel 252. The hologram device 264 may show a three dimensional (3D) image in the air by using an interference of light. The projector 266 may project light onto a screen to display an image. The screen may be located, for example, in the interior of or on the exterior of the electronic device 201. According to an embodiment of the present disclosure, the display 260 may further include a control circuit for controlling the panel 262, the hologram device 264, or the projector 266.

The interface 270 may include, for example, a High-Definition Multimedia Interface (HDMI) 272, a Universal Serial Bus (USB) 274, an optical interface 276, or a D-sub-miniature (D-sub) 278. The interface 270 may be included in, for example, the communication interface 170 illustrated in FIG. 1. Additionally or alternatively, the interface 270 may include, for example, a Mobile High-definition Link (MHL) interface, a Secure Digital (SD) card/Multi-Media Card (MMC) interface, or an Infrared Data Association (IrDA) standard interface.

The audio module 280, for example, may bilaterally convert a sound and an electrical signal. At least some components of the audio module 280 may be included in, for example, the input/output interface 150 illustrated in FIG. 1. The audio module 280 may process voice information input or output through, for example, a speaker 282, a receiver 284, earphones 286, or the microphone 288.

The camera module 291 is, for example, a device which may photograph a still image and a video. According to an embodiment of the present disclosure, the camera module 291 may include one or more image sensors (e.g., a front sensor or a back sensor), a lens, an Image Signal Processor (ISP) or a flash (e.g., LED or xenon lamp).

The power management module 295 may manage, for example, power of the electronic device 201. According to an embodiment of the present disclosure, the power management module 295 may include a Power Management Integrated Circuit (PMIC), a charger Integrated Circuit (IC), or a battery or fuel gauge. The PMIC may use a wired and/or wireless charging method. Examples of the wireless charging method may include, for example, a magnetic resonance method, a magnetic induction method, an electromagnetic wave method, and the like. Additional circuits (e.g., a coil loop, a resonance circuit, a rectifier, etc.) for wireless charging may be further included. The battery gauge may measure, for example, a residual quantity of the battery 296, and a voltage, a current, or a temperature while charging. The battery 296 may include, for example, a rechargeable battery and/or a solar battery.

The indicator 297 may display a particular state (e.g., a booting state, a message state, a charging state, or the like) of the electronic device 201 or a part (e.g., the processor 210) of the electronic device 201. The motor 298 may convert an electrical signal into a mechanical vibration, and may generate a vibration, a haptic effect, or the like. Although not illustrated, the electronic device 201 may include a processing device (e.g., a GPU) for supporting a mobile TV. The processing device for supporting a mobile TV may process, for example, media data according to a certain standard such as Digital Multimedia Broadcasting (DMB), Digital Video Broadcasting (DVB), or media-FLO®.

Each of the above-described component elements of hardware according to the present disclosure may be configured with one or more components, and the names of the corresponding component elements may vary based on the type of electronic device. In various embodiments, the electronic device may include at least one of the above-described elements. Some of the above-described elements may be omitted from the electronic device, or the electronic device may further include additional elements. Also, some of the hardware components according to various embodiments may be combined into one entity, which may perform functions identical to those of the relevant components before the combination.

Figure 3:
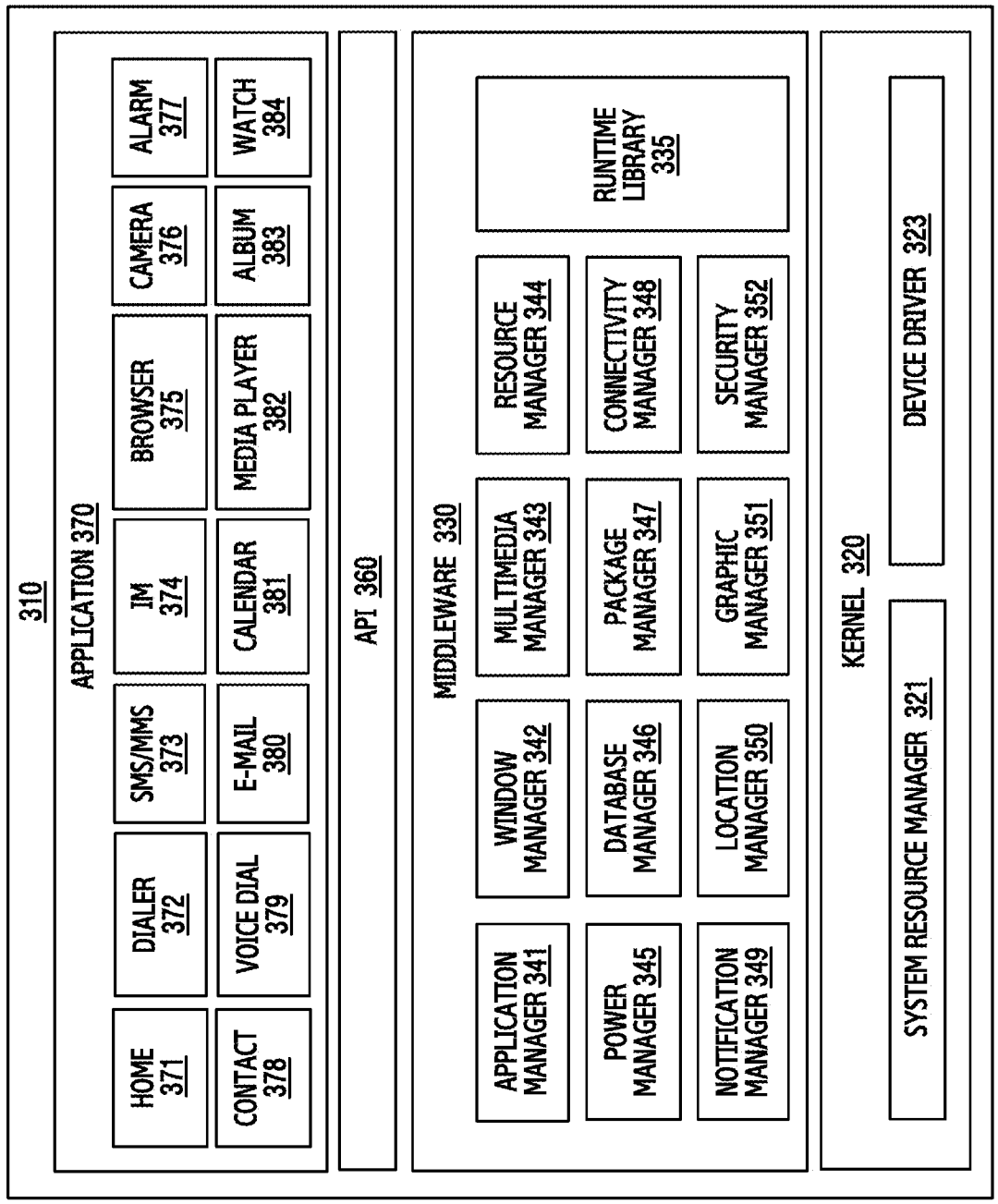
FIG. 3 illustrates a block diagram of a program module according to various embodiments.

FIG. 3 illustrates a block diagram of a program module according to various embodiments of the present disclosure.

According to an embodiment of the present disclosure, the program module 310 (e.g., the program 140) may include an Operating System (OS) for controlling resources related to the electronic device (e.g., the electronic device 101) and/or various applications (e.g., the application programs 147) executed in the operating system. The operating system may be, for example, Android®, iOS®, Windows®, Symbian®, Tizen®, Bada®, or the like.

The program module 310 may include a kernel 320, middleware 330, an API 360, and/or applications 370. At least some of the program module 310 may be preloaded on an electronic device, or may be downloaded from an external electronic device (e.g., the electronic device 102 or 104, or the server 106).

The kernel 320 (e.g., the kernel 141) may include, for example, a system resource manager 321 and/or a device driver 323. The system resource manager 321 may control, allocate, or collect system resources. According to an embodiment of the present disclosure, the system resource manager 321 may include a process management unit, a memory management unit, a file system management unit, and the like. The device driver 323 may include, for example, a display driver, a camera driver, a Bluetooth® driver, a shared memory driver, a USB driver, a keypad driver, a Wi-Fi driver, an audio driver, or an Inter-Process Communication (IPC) driver.

For example, the middleware 330 may provide a function used in common by the applications 370, or may provide various functions to the applications 370 through the API 360 so as to enable the applications 370 to efficiently use the limited system resources in the electronic device. According to an embodiment of the present disclosure, the middleware 330 (e.g., the middleware 143) may include at least one of a run time library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, and a security manager 352.

The runtime library 335 may include a library module that a compiler uses in order to add a new function through a programming language while an application 370 is being executed. The runtime library 335 may perform input/output management, memory management, the functionality for an arithmetic function, or the like.

The application manager 341 may manage, for example, a life cycle of at least one of the applications 370. The window manager 342 may manage Graphical User Interface (GUI) resources used by a screen. The multimedia manager 343 may recognize a format used for reproduction of various media files, and may perform encoding or decoding of a media file by using a codec suitable for the corresponding format. The resource manager 344 may manage resources of a source code, a memory, and a storage space of at least one of the applications 370.

The power manager 345 may operate together with, for example, a Basic Input/Output System (BIOS) or the like to manage a battery or power source and may provide power information or the like used for the operations of the electronic device. The database manager 346 may generate, search for, and/or change a database to be used by at least one of the applications 370. The package manager 347 may manage installation or an update of an application distributed in a form of a package file.

For example, the connectivity manager 348 may manage wireless connectivity such as Wi-Fi or Bluetooth. The notification manager 349 may display or notify of an event such as an arrival message, promise, proximity notification, and the like in such a way that does not disturb a user. The location manager 350 may manage location information of an electronic device. The graphic manager 351 may manage a graphic effect which will be provided to a user, or a user interface related to the graphic effect. The security manager 352 may provide all security functions used for system security, user authentication, or the like. According to an embodiment of the present disclosure, when the electronic device (e.g., the electronic device 101) has a telephone call function, the middleware 330 may further include a telephony manager for managing a voice call function or a video call function of the electronic device.

The middleware 330 may include a middleware module that forms a combination of various functions of the above-described components. The middleware 330 may provide a module specialized for each type of OS in order to provide a differentiated function. Further, the middleware 330 may dynamically remove some of the existing components or add new components.

The API 360 (e.g., the API 145) is, for example, a set of API programming functions, and may be provided with a different configuration according to an OS. For example, in the case of Android or iOS, one API set may be provided for each platform. In the case of Tizen, two or more API sets may be provided for each platform.

The applications 370 (e.g., the application programs 147) may include, for example, one or more applications which may provide functions such as a home 371, a dialer 372, an SMS/MMS 373, an Instant Message (IM) 374, a browser 375, a camera 376, an alarm 377, contacts 378, a voice dial 379, an email 380, a calendar 381, a media player 382, an album 383, a clock 384, health care (e.g., measuring exercise quantity or blood sugar), or environment information (e.g., providing atmospheric pressure, humidity, or temperature information).

According to an embodiment of the present disclosure, the applications 370 may include an application (hereinafter, referred to as an "information exchange application" for convenience of description) that supports exchanging information between the electronic device (e.g., the electronic device 101) and an external electronic device (e.g., the electronic device 102 or 104). The information exchange application may include, for example, a notification relay application for transferring specific information to an external electronic device or a device management application for managing an external electronic device.

For example, the notification relay application may include a function of transferring, to the external electronic device (e.g., the electronic device 102 or 104), notification information generated from other applications of the electronic device 101 (e.g., an SMS/MMS application, an e-mail application, a health management application, or an environmental information application). Further, the notification relay application may receive notification information from, for example, an external electronic device and provide the received notification information to a user.

The device management application may manage (e.g., install, delete, or update), for example, at least one function of an external electronic device (e.g., the electronic device 102 or 104) communicating with the electronic device (e.g., a function of turning on/off the external electronic device itself (or some components) or a function of adjusting the brightness (or a resolution) of the display), applications operating in the external electronic device, and services provided by the external electronic device (e.g., a call service or a message service).

According to an embodiment of the present disclosure, the applications 370 may include applications (e.g., a health care application of a mobile medical appliance or the like) designated according to an external electronic device (e.g., attributes of the electronic device 102 or 104). According to an embodiment of the present disclosure, the applications 370 may include an application received from an external electronic device (e.g., the server 106, or the electronic device 102 or 104). According to an embodiment of the present disclosure, the applications 370 may include a preloaded application or a third party application that may be downloaded from a server. The names of the components of the program module 310 of the illustrated embodiment of the present disclosure may change according to the type of operating system.

According to various embodiments, at least a part of the programming module 310 may be implemented in software, firmware, hardware, or a combination of two or more thereof. At least some of the program module 310 may be implemented (e.g., executed) by, for example, the processor (e.g., the processor 1410). At least some of the program module 310 may include, for example, a module, a program, a routine, a set of instructions, and/or a process for performing one or more functions.

The term "module" as used herein may, for example, mean a unit including one of hardware, software, and firmware or a combination of two or more of them. The "module" may be interchangeably used with, for example, the term "unit", "logic", "logical block", "component", or "circuit". The "module" may be a unit of an integrated component element or a part thereof. The "module" may be a unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter.

According to various embodiments, at least some of the devices (for example, modules or functions thereof) or the method (for example, operations) according to the present disclosure may be implemented by a command stored in a computer-readable storage medium in a programming module form. The instruction, when executed by a processor (e.g., the processor 120), may cause the one or more processors to execute the function corresponding to the instruction. The computer-readable recoding media may be, for example, the memory 130.

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high class language codes, which can be executed in a computer by using an interpreter, as well as machine codes made by a compiler. The aforementioned hardware device may be configured to operate as one or more software modules in order to perform the operation of the present disclosure, and vice versa.

FIGS. 1 to 2 may correspond to a first electronic device or a second electronic device.

Figure 4:
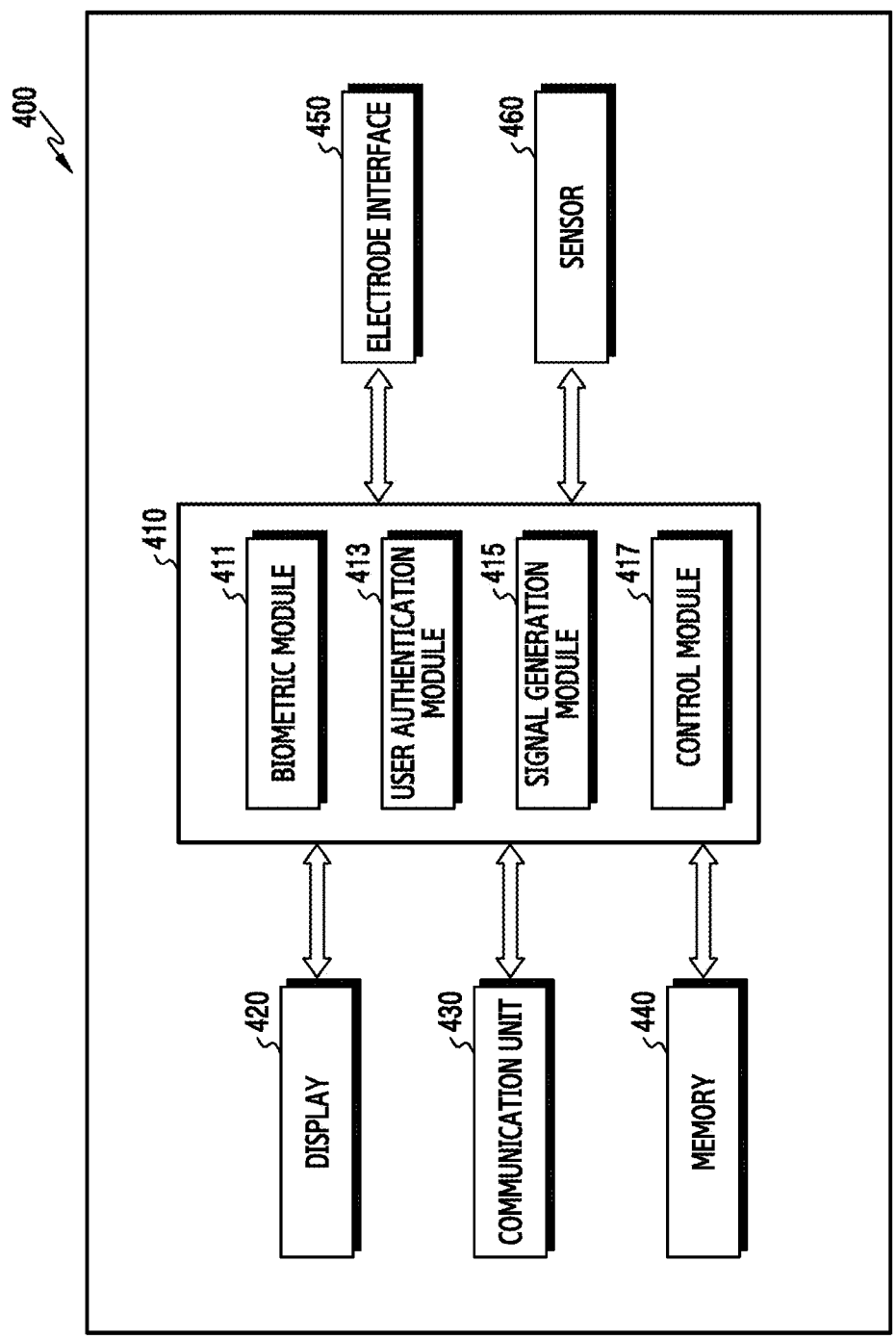
FIG. 4 illustrates a block diagram of the configuration of a first electronic device according to various embodiments.

FIG. 4 illustrates a block diagram showing the configuration of a first electronic device according to various embodiments.

Referring to FIG. 4, a first electronic device 400 may include a processor 410, a display 420, a communication unit 430, a memory 440, an electrode interface 450, and a sensor 460. The first electronic device 400 according to various embodiments does not necessarily include the components shown in FIG. 4, so the first electronic device 400 may include more or fewer components than those shown in FIG. 4. The first electronic device 400 according to various embodiments may be a device such as a wearable device that can be worn on the body of a user.

According to various embodiments, the electrode interface 450 may include one or more electrodes. Since the electrode interface 450 is included in the first electronic device 400, the electrode interface 450 may be interpreted as a first electrode interface. The electrode interface 450 may be brought in direct or indirect contact with the body of a user. Various measurement signals can be received, depending on the contact types of the electrode interface 450 on the body of a user or the number of the electrode interface 450. For example, the electrode interface 450 can transmit a current signal having a predetermined frequency to the body of a user and can obtain a measurement signal from a measured pulse or by measuring impedance. For example, the measurement signal may include at least one of an ECG (electrocardiography) signal, a BIA (Body impedance analysis) signal, and a GSR (galvanic skin reflex) signal.

According to various embodiments, when a sensor for obtaining heartbeat information is an ECG sensor, the electrode interface 450 may be composed of a first electrode set and a second electrode set. The electrode interface 450 can obtain an ECG signal by measuring voltages applied to the worn electrodes from bioelectrical signals generated for heartbeat. As another example, the electrode interface 450 can measure impedance by applying a current with a specific frequency between the first electrode set and the second electrode set to measure a BIA signal and by measuring the voltage between the first electrode set and the second electrode set. Alternatively, the electrode interface 450 can measure impedance by applying a specific voltage to the first electrode set and the second electrode set to receive a GSR signal.

According to various embodiments, the sensor 460 can continuously or periodically sense information detected from a user. Since the sensor 460 is included in the first electronic device 400, the sensor 460 may be interpreted as a first sensor. The sensor 460 may include at least one of an acceleration sensor, a gyro sensor, a geomagnetic sensor, and a barometric pressure sensor. Alternatively, the sensor 460 may include a biometric sensor, a fingerprint sensor, or an iris sensor. The biometric sensor may be at least any one of an optical sensor, an ECG sensor, and a PPG sensor. When the sensor for obtaining heartbeat information is an optical sensor, the sensor 460 may be composed of a light emission element and a light reception element. The light emission element may be at least any one of an IR (infrared) LED, a Red LED, a Green LED, and a Blue LED and the light reception element may be a photodiode. When the first electronic device 400 is brought in contact with (or attached to or worn on) the body of a user, the light emission element can emit light and the light reception element can detect the light reflected back by at least a portion of the body of the user after emitted from the light emission element. For example, the light may penetrate deeper than the skin of a user (for example, to a blood vessel) and then be reflected out to determine a variation in blood stream of the user. The light reception element can generate a measurement signal by quantifying and sequentially arranging the detected amounts of light.

According to various embodiments, when the biometric sensor is a PPG sensor, the PPG sensor may use the principle that the degrees of absorbing and reflecting light depend on a change in thickness of a blood vessels due to the heartbeat. The PPG sensor may be composed of a light emission element that emits infrared light and a light reception element that senses light emitted from the light emission element and then reflected from the body of a user. The magnitude of the value measured by the light reception element depends on the amount of blood stream that is changed by the heartbeat and a PPG (Photoplethysmography) signal can be obtained by measuring the changing period. If the PPG sensor includes a light emission element having two wavelengths, it is possible to measure oxygen saturation in addition to the heartbeat. The sensor 460 can transmit the measured sensing data to the processor 410.

According to various embodiments, the processor 410 can generate a user authentication signal on the basis of user information obtained through user authentication and transmit the generated user authentication signal to the electrode interface 450. Since the processor 410 is included in the first electronic device 400, the processor 410 may be interpreted as a first processor. The processor 410 can measure biometric information, using a measurement signal obtained from the electrode interface 450 or the sensor 460 (for example, a biometric sensor, a fingerprint sensor, and an iris sensor), can perform user authentication by comparing the measured biometric information with biometric information stored in the memory 440, and can generate a user authentication signal using user information when the user authentication is completed. Alternatively, the processor 410 may perform user authentication, using a password or a lock pattern through a keypad (or a keyboard). To this end, the processor 410 may include a biometric module 411, a user authentication module 413, a signal generation module 415, and a control module 417.

According to various embodiments, the biometric module 411 can receive a measurement signal generated by measuring the body of a user from the electrode interface 450 or the sensor 460 being in contact with the body of the user and can obtain biometric information using the received measurement signal. For example, the measurement signal may include at least one of an ECG signal, a PPG signal, a BIA signal, and a GSR signal. The biometric module 411 can obtain at least one of heartbeat information, oxygen saturation information, body fat information, and stress information, using the measurement signal. For example, the ECG signal or the PPG signal may be obtained by measuring potential that is generated in relation to heartbeat on the surface of the skin of a user. The biometric module 411 can obtain heartbeat information of a user, using the ECG signal. The biometric module 411 can receive the ECG signal from the electrode interface 450 by selectively using the electrode interface 450.

According to various embodiments, the BIA signal may be obtained by measuring resistance between electrodes after applying a fine current into the body of a user. On the basis of the BIA signal, it is possible to measure the resistance value in the body by measuring the voltage value between the electrode interfaces 450. The biometric module 411 can obtain body fat information of the body of a user, using the BIA signal. The GSR signal, which is used for a galvanic skin reflex that is one type of autonomic function test, can be measured using two adjacent electrodes. The biometric module 411 can obtain stress information by using the GSR signal. The biometric module 411 can transmit the obtained biometric information to the user authentication module 413.

According to various embodiments, the user authentication module 413 can perform user authentication using the biometric information obtained from the biometric module 411. The user authentication module 413 can compare the biometric information obtained from the biometric module 411 with biometric information stored in the memory 440. When the obtained biometric information is the same as the stored biometric information, the user authentication module 413 can determine that the obtained biometric information belongs to the user and complete (for example, succeed or allow) user authentication. When the obtained biometric information is not the same as the stored biometric information, the user authentication module 413 can determine that the obtained biometric information does not belong to the user and disallow (for example, fail) user authentication. When user authentication is completed, the user authentication module 413 can transmit authentication completion to the signal generation module 415. Alternatively, the user authentication module 413 can transmit the authentication result (for example, success or failure) to the signal generation module 415. Alternatively, the user authentication module 413 may perform user authentication using a password or a lock pattern.

According to various embodiments, the signal generation module 415 can generate a user authentication signal, using the user information when user authentication is completed by the user authentication module 413. The user information may include at least one of the user accountant of the first electronic device 400, the phone number of the first electronic device 400, and information about the user (for example, name, age, height, and weight). The user information can be stored in the memory 440. The signal generation module 415 can select at least one signal pattern on the basis of the user information and generate a specific current for user authentication at a specific frequency band using the selected signal pattern. The specific current generated in this way may be a user authentication signal. The signal pattern may be different for each user and may be changed by at least one of time information, position information, or sequence information.

According to various embodiments, the control module 417 can control the user authentication signal or a signal including at least a portion of the user authentication signal to be applied to the electrode interface 450. The control module 417 can control the user authentication signal or a signal including at least a portion of the user authentication signal to be transmitted to the electrode interface 450 such that the user authentication signal is applied to the body. (The entire or A portion of) the user authentication signal may be transmitted independently to the electrode interface 450 or may be included in another signal (for example, a control signal) and transmitted with the signal to the electrode interface 450. The control module 417 can store the biometric information obtained from the biometric module 411 in the memory 440. The control module 417 can store the biometric information in the memory 440 together with a user authentication signal. According to various embodiments, the memory 440 can store biometric information, user information, and a user authentication signal in a security section.

According to various embodiments, the control module 417 can transmit biometric information to a server or another electronic device through the communication unit 430. For example, the communication unit 430 can transmit biometric information including the user authentication signal stored in the memory 440 to a server or another electronic device, using at least one communication method (for example, BT, Wifi, NFC, and Cellular). The communication unit 430 may be a communication module 220 of FIG. 2. The communication unit 430 can obtain position information of the first electronic device 400 using a GNSS module.

According to various embodiments, the display 420 can display various items of information related to at least one of biometric information, user information, and biometric information including a user authentication signal. For example, the display 420 can display biometric information, user information, and a user authentication signal in detail or in order of time on the basis of user input (for example, touch input or button/key/wheel input) The display 420 may be a display 260 of FIG. 2.

According to various embodiments, the processor 410 may be composed of a first processor and a second processor. The first processor may operate (for example, enter an activation state or an operation mode) when the first electronic device 400 is powered. The first processor can wake up, receive a measurement signal from the electrode interface 450, and receive sensing data from the sensor 460 while the first electronic device 400 is powered. The first processor may be in a wake-up state regardless of turning-on/off of the display 420 of the first electronic device 400. The first processor can be operated by lower power than the second processor. The first processor can transmit periodically or in real time the measurement signal or the sensing data to the second processor.

According to various embodiments, the second processor can be selectively operated. For example, the second processor can operate in an activation state (for example, an operation mode) when the display 420 is turned on, obtains information, or scans information. Further, the second processor can operate in an inactivation state (for example, a sleep mode) when the display 420 is turned off. That is, the second processor can wake up and operate in the activation state when operating in the inactivation state (for example, a sleep mode) in accordance with at least a period, a set scan period, and an operation period of an application (or an information request of an application).

The biometric module 411, user authentication module 413, signal generation module 415, and control module 417 according to various embodiments, which are command sets or codes stored in the memory 440, may be commands/codes at least temporarily residing in the processor 410, storage spaces storing commands/codes, or portions of a circuit constituting the processor 410.

Figure 5:
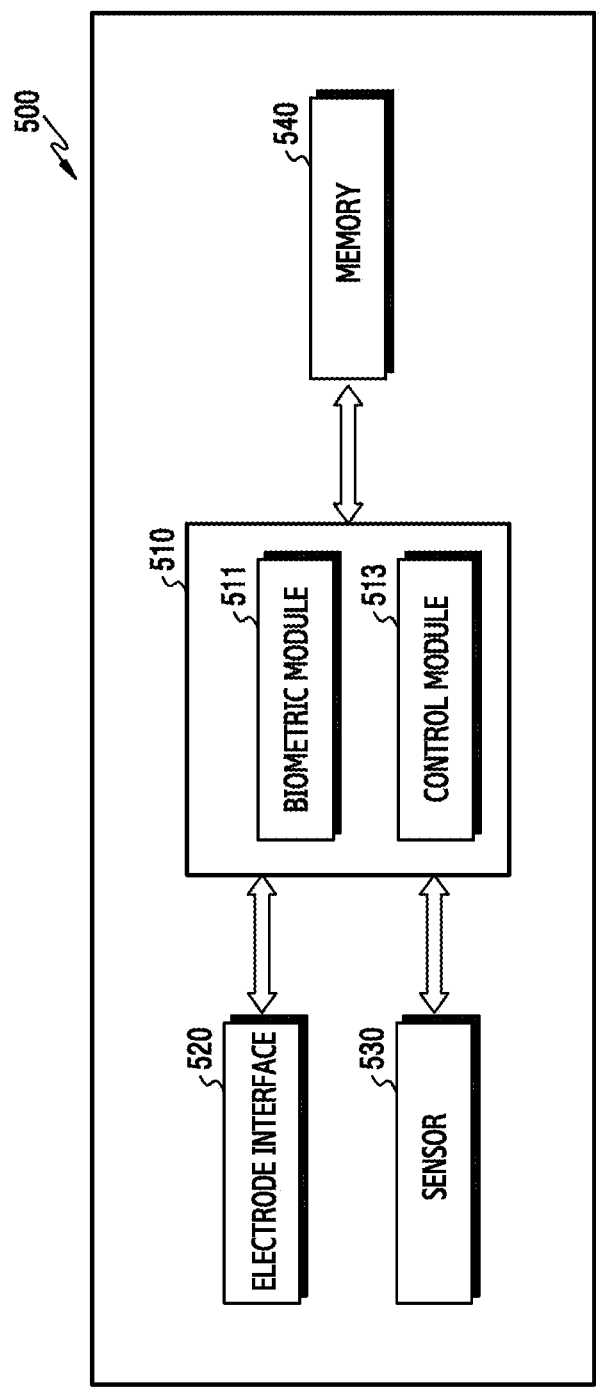
FIG. 5 illustrates a block diagram of the configuration of a second electronic device according to various embodiments.

FIG. 5 illustrates a block diagram of the configuration of a second electronic device according to various embodiments.

Referring to FIG. 5, a second electronic device 500 may include a processor 510, an electrode interface 520, a sensor 530, and a memory 540. The second electronic device 500 according to various embodiments does not necessarily include the components shown in FIG. 5, so the electronic device 500 may include more or fewer components than those shown in FIG. 5. The electronic device 500 according to various embodiments may be a pad or a patch that can be attached to or brought in contact with the body of a user.

According to various embodiments, the electrode interface 520 may include one or more electrodes. Since the electrode interface 520 is included in the second electronic device 500, the electrode interface 520 may be interpreted as a second electrode interface. The electrode interface 520 may be directly or indirectly brought contact with or attached to the body of a user. Various measurement signals can be received, depending on the contact types of the electrode interface 520 on the body of a user or the number of the electrode interface 520. For example, the electrode interface 520 can transmit a current signal having a predetermined frequency to the body of a user and can obtain a measurement signal from a measured pulse or by measuring impedance. For example, the measurement signal may include at least one of an ECG signal, a BIA signal, and a GSR signal. The electrode interface 520 is the same as or similar to the electrode interface 450 of FIG. 4, so a detailed description may not be provided.

According to various embodiments, the sensor 530 can continuously or periodically sense information from a user. Since the sensor 530 is included in the second electronic device 500, the sensor 530 may be interpreted as a second sensor. The sensor 530 may be a biometric sensor. The biometric sensor may be at least any one of an optical sensor, an ECG sensor, and a PPG sensor. The sensor 530 can transmit the measured sensing data to the processor 510. The sensor 530 is the same as or similar to the sensor 460 of FIG. 4, so the detailed description may not be provided.

According to various embodiments, the processor 510 (for example, a micro controller unit (MCU)) can apply a measurement signal to the electrode interface 520 and receive and store a user authentication signal or a signal including at least a portion of a user authentication signal in the memory 540. Since the processor 510 is included in the second electronic device 500, the processor 510 may be interpreted as a second processor. The processor 510 can measure biometric information, using a measurement signal obtained from the electrode interface 520 or the sensor 530, and store the measured biometric information in the memory 540. To this end, the processor 510 may include a biometric module 511 and a control module 513.

According to various embodiments, the biometric module 511 can receive a measurement signal (for example, a second measurement signal) generated by measuring the body of a user from the electrode interface 520 or the sensor 530 being in contact with the body of the user and can obtain biometric information (for example, second biometric information) using the received measurement signal. For example, the measurement signal may include at least one of an ECG signal, a PPG signal, a BIA signal, and a GSR signal. The biometric module 511 can obtain at least one of heartbeat information, oxygen saturation information, body fat information, and stress information, using the measurement signal. The biometric module 511 can transmit the obtained biometric information to the control module 513.

According to various embodiments, the control module 513 can store the biometric information in the memory 540. The control module 513 can receive a user authentication signal or a signal including at least a portion of the user authentication signal through the body. The control module 513 can store the biometric information in the memory 540 together with a user authentication signal. According to various embodiments, the memory 540 can store biometric information, a user authentication signal, or at least a portion of a user authentication signal.

An electronic device 400 according to various embodiments includes an electrode interface 450 that can be brought in contact with the body of a user, a memory 440, and a processor 410 operably coupled to the electrode interface and the memory. The processor can be set to obtain user information through user authentication, to generate a user authentication signal on the basis of the user information, and to transmit the user authentication signal or a signal including at least a portion of the user authentication signal through the body of the user being in contact with the electrode interface.

The electronic device may further include a sensor that obtains biometric information and the processor can be set to obtain at least one item of biometric information using the sensor or the electrode interface and to perform user authentication using the at least one item of biometric information.

The processor can be set to perform user authentication by comparing the at least one item of biometric information with biometric information stored in the memory, and to generate the user authentication signal on the basis of user information when the user authentication is completed.

The processor can be set to complete user authentication when the at least one item of biometric information is the same as the biometric information stored in the memory.

The processor can be set to select at least one signal pattern on the basis of the user information and to generate a specific current for user authentication as the user authentication signal at a specific frequency band using the selected signal pattern.

The signal pattern may be set to have different patterns for each user or to be changed in accordance with the device information of the electronic device.

The device information may include at least one of time information, position information, and sequence information, and the processor can be set to change the frequency of the signal pattern using the device information.

The processor can be set to transmit the user authentication signal or a signal including at least a portion of the user authentication signal to another electronic device being in contact with the body of the user.

The processor can be set to associate and store the obtained biometric information with the user authentication signal in the memory.

The processor can be set to receive another biometric information measured by the other electronic device through the electrode interface.

The electronic device may further include a communication interface (a communication unit 430) or an interface 270 and the processor can be set to receive another biometric information measured by the other electronic device through the communication interface.

The processor can be set to determine whether the user authentication signal is included in the other biometric information, and to store the received another biometric information in the memory when the user authentication signal is included in the other biometric information.

An electronic device 500 that is brought in contact with a body according to various embodiments may include an electrode interface 520 that can be brought in contact with the body of a user, a memory 540, and a processor (MCU) 510 operably coupled to the electrode interface and the memory. The processor 510 can be set to obtain biometric information using the electrode interface, to receive a user authentication signal or a signal including at least a portion of the user authentication signal from the electrode interface, and to store the obtained biometric information in the memory together with the user authentication signal.

The processor 510 can be set to receive a control signal from the electrode interface and to apply a measurement signal for obtaining at least one item of biometric information to the electrode interface on the basis of the control signal.

The electronic device may further include a communication interface and the processor 510 can be set, when receiving a control signal from the communication interface, to transmit at least one item of biometric information including the user authentication signal stored in the memory to another electronic device through the communication interface.

A system according to various embodiments may include: a first electronic device 400 that generates a user authentication signal on the basis of user information obtained through user authentication and transmits the user authentication signal or a signal including at least a portion of the user authentication signal through the body of a user being in contact with a first electrode interface 450; and a second electronic device 500 that obtains at least one item of biometric information using a second electrode interface, receives a user authentication signal or a signal including at least a portion of the user authentication signal from the second electrode interface, and stores the at least one item of biometric information in a memory together with the user authentication signal.

The first electronic device 400 can be set to obtain at least one item of biometric information using a biometric sensor or the first electrode interface, to perform user authentication using the at least one item of biometric information, and to generate the user authentication signal when the user authentication is completed.

The first electronic device 400 can be set to select at least one signal pattern on the basis of the user information and to generate a specific current for user authentication as the user authentication signal at a specific frequency band using the selected signal pattern.

The first electronic device 400 can be set to transmit the user authentication signal or a signal including at least a portion of the user authentication signal to the second electronic device being in contact with the body of the user through the first electrode interface.

The first electronic device 400 and the second electronic device 500 can be set to obtain the same biometric information or different biometric information.

The first electronic device 400 can be set to apply a detection signal to the first electrode interface, and to determine that the second electronic device is in contact with the body of the user when noise is included in a signal received by the detection signal.

Figure 6:
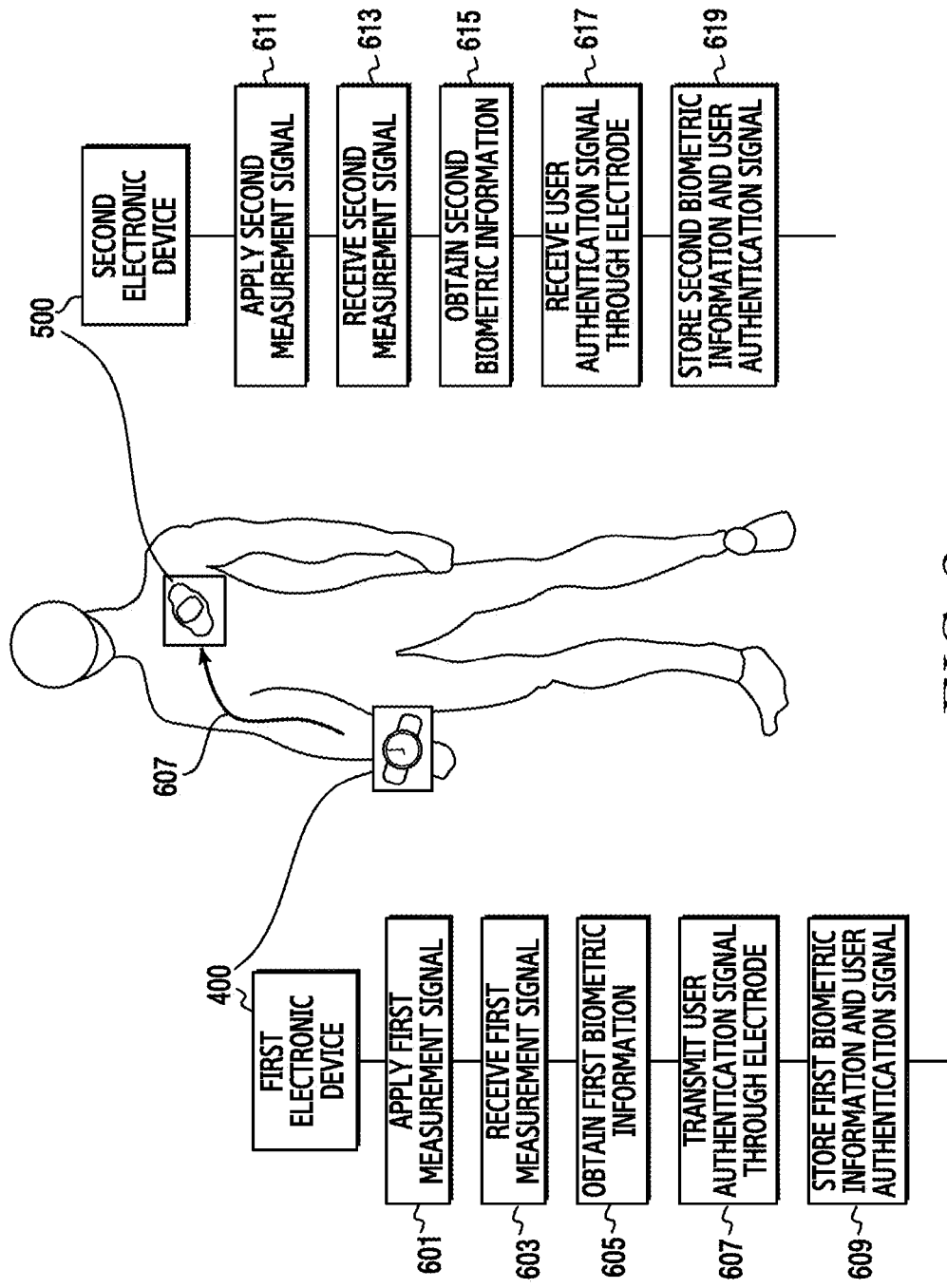
FIG. 6 illustrates a diagram of an example of obtaining user authentication-biometric information through an electronic device being in contact with the body of a user according to various embodiments.

FIG. 6 illustrates a diagram of an example of obtaining user authentication-biometric information through an electronic device being in contact with the body of a user according to various embodiments.

Referring to FIG. 6, the first electronic device 400 and the second electronic device 500 may be in contact with (or worn on) the body of a user. For the convenience of description, the first electronic device 400 can be considered as a device that can generate a user authentication signal and the second electronic device 500 can be considered as a device (or a sensor) that can measure biometric information. That is, the second electronic device 500 may be a device that can only measure biometric information, unlike the first electronic device 400. In this case, the second electronic device 500 does not perform another function except for measuring biometric information, so the second electronic device 500 may consume less power than the first electronic device 400. Further, a signal (for example, a first measurement signal) or information (for example, first biometric information) by the first electronic device 400 and a signal (for example, a second measurement signal) or information (for example, second biometric information) by the second electronic device 500 may be discriminated by "first" or "second". The electronic device 400 can transmit a user authentication signal through the body of the user without a process of pairing with the second electronic device 500. Further, although one second electronic device 500 is shown in FIG. 5, one or more second electronic devices 500 may be provided. However, embodiments of the present disclosure are limited to the description.

In operation 601, the first electronic device 400 according to various embodiments can apply a first measurement signal to measure biometric information. For example, the first electronic device 400 can apply the first measurement signal through an electrode interface 450. The first measurement signal may be to apply a fine current to the body. The first measurement signal may include at least one of an ECG signal, a BIA signal, and a GSR signal. Different measurement signals may be applied, depending on biometric information to be measured. Further, the first electronic device 400 can selectively use the electrode interface 450, depending on measurement signals. Alternatively, the first electronic device 400 can apply the first measurement signal through a light emission element of a sensor 460.

In operation 603, the first electronic device 400 according to various embodiments can receive the first measurement signal. For example, the first electronic device 400 can receive a voltage value measured from the current applied to the body or a resistance value of the body as the first measurement signal. Different measurement signals may be received, depending on biometric information to be measured. For example, the first electronic device 400 can receive potential present on the skin surface of the user in relation to heartbeat as the first measurement signal. Alternatively, the first electronic device 400 can receive a BIA signal obtained by measuring the resistance value of the body as the first measurement signal by measuring a voltage value between the electrode interfaces 450.

In operation 605, the first electronic device 400 according to various embodiments can obtain first biometric information using the received first measurement signal. The first biometric information may include at least one of heartbeat information, oxygen saturation information, body fat information, and stress information. The first electronic device 400 can determine whether the obtained first biometric information is the same as biometric information stored in a memory 440. The first electronic device 400 can generate a user authentication signal using user information when the obtained first biometric information is the same as the biometric information stored in the memory 440. For example, the first electronic device 400 can select at least one signal pattern on the basis of the user information of the user of the first electronic device 400 and generate a specific current for user authentication as the user authentication signal at a specific frequency band using the selected signal pattern. The biometric information obtained using the sensor 460 may be fingerprint information, iris information, and heartbeat information. The first electronic device 400 according to various embodiments may perform user authentication using a fingerprint sensor or an iris sensor. The first electronic device 400 according to various embodiments may perform user authentication using a password or a lock pattern other than the biometric information.

The first electronic device 400 according to various embodiments can obtain first biometric information for a predetermined time by repeatedly performing the operations 601 to 605. When obtaining one item of first biometric information (for example, initial first biometric information), the first electronic device 400 can generate the user authentication signal.

In operation 607, the first electronic device 400 according to various embodiments can apply the generated user authentication signal to the electrode interface 450. The user authentication signal applied to the electrode interface 450 can be transmitted to the second electronic device 500 through the body. The electrode interface 450 can apply a current for the user authentication signal, similar to a measurement signal, to the body. The first electronic device 400 can apply the entire or a portion of the user authentication signal to the electrode interface 450. The first electronic device 400 according to various embodiments can apply the user authentication signal to the electrode interface 450 together with other signals (for example, a control signal, a detection signal, and a measurement signal).

In operation 609, the first electronic device 400 according to various embodiments can store the first biometric information and the user authentication signal in the memory 440. The memory 440 can separately store the first biometric information and the user authentication signal or can combine and store the first biometric information and the user authentication signal in one set. The first biometric information stored in the memory 440 can be authenticated or proved as being measured from the user of the first electronic device 400 by the user authentication signal. The first electronic device 400 can display the first biometric information of the user authentication signal stored in the memory 440 through a display 420. The first electronic device 400 may store the entire or a portion of the user authentication signal when storing the user authentication signal in the memory 440.

The first electronic device 400 according the various embodiments can generate notification associated with an error message when the first biometric information is different from registered biometric information (for example, biometric information stored in the memory 440) or when this situation can be suspected. For example, the first electronic device 400 can display a user interface including an error message (for example, "Unauthenticated user, Please authenticate again!) on the display 420. In this case, the first electronic device 400 can request a procedure for user authentication through the error message. When receiving user information through at least one other electronic device (for example, the second electronic device 500 or a server), the first electronic device 400 according to various embodiments can inform the user that the user information has been received. The first electronic device 400 can inform the user of various items of information such as whether there is another electronic device (for example, the second electronic device 500) that is measuring information, the number of other electronic devices, and information that is being measured.

In operation 611, the second electronic device 500 according to various embodiments can apply a second measurement signal to measure biometric information. The second electronic device 500 may be a device (or a sensor) that can obtain only one item of biometric information or one or more items of biometric information related to the body. Alternatively, the second electronic device 500 may be a device that obtains biometric information similar to or the same as, or different from the biometric information obtained by the first electronic device 400. For example, the second electronic device 500 can apply the second measurement signal through an electrode. The second measurement signal may be to apply a fine current to the body. The second measurement signal may include at least one of an ECG signal, an EMG (electromyography) signal, an EEG (sleep electroencephalogram) signal, a BIA signal, and a GSR signal.

In operation 613, the second electronic device 500 according to various embodiments can receive the second measurement signal. For example, the second electronic device 500 can receive a voltage value measured from the current applied to the body or a resistance value of the body as the second measurement signal. Different measurement signals may be received, depending on biometric information to be measured.

In operation 615, the second electronic device 500 according to various embodiments can obtain second biometric information using the received second measurement signal. The second biometric information may include at least one of heartbeat information, oxygen saturation information, electromyogram information, electroencephalogram information, body fat information, and stress information.

The second electronic device 500 according to various embodiments can obtain second biometric information for a predetermined time by repeatedly performing the operations 611 to 615.

In operation 617, the second electronic device 500 according to various embodiments can receive a user authentication signal or a signal including at least a portion of a user authentication signal. The second electronic device 500 according to various embodiments can receive the user authentication signal in operations 611 to 615. That is, the operation 617 may be performed after the operations 611 to 615 or in operations 611 to 615.

In operation 619, the second electronic device 500 according to various embodiments can store the second biometric information and the user authentication signal. The second electronic device 500 may include an electrode that applies/receives a second measurement signal for measuring biometric information, a measuring module that obtains second biometric information using the second measurement signal, a memory that stores the second biometric information, and a processor (for example, a micro controller unit (MCU)) that controls the electrode, the measuring module, and the memory. The second electronic device 500 can separately store the second biometric information and the user authentication signal or can combine and store the second biometric information and the user authentication signal in one set. The second biometric information stored in the memory can be authenticated or proved as being measured from the user of the first electronic device 400 by the user authentication signal.

The operations 601 to 605 may be performed simultaneously with or before the operations 611 to 615. This is only a matter associated with implementation and the present disclosure is not limited thereto.

The first electronic device 400 according to various embodiments may perform reciprocal authentication in combination with the second electronic device 500. The first electronic device 400 can transmit a first specific signal pattern to the second electronic device 500 and the second electronic device 500 can transmit a second specific signal pattern to the first electronic device 400. For example, when a user wears a watch-type wearable device (for example, the first electronic device 400) having user authentication-biometric information (for example, information such as vein pattern/blood stream pattern) and a predetermined high-frequency pattern synchronized with a heartbeat measurement period of a necklace-type wearable device (for example, the second electronic device 500) is generated by the watch-type wearable device, the second electronic device 500 can prove that the second biometric information thereof is biometric information measured from the body of the same user by measuring heartbeat and receiving and storing the corresponding high-frequency pattern. The first electronic device 400 according to various embodiments can receive the second biometric information from the second electronic device 500 and can monitor from whom the second biometric information was measured. The second electronic device 500 according to various embodiments can store only the second biometric information in the memory when the second electronic device 500 does not receive the user authentication signal.

Figure 7:
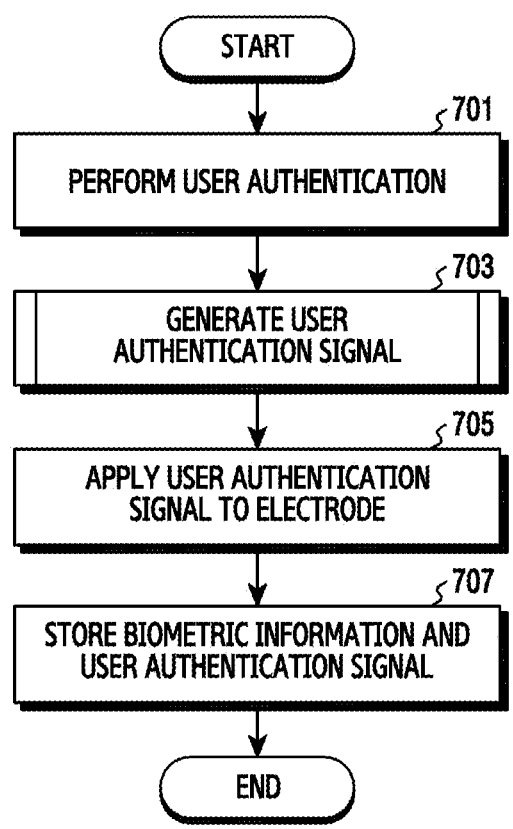
FIG. 7 illustrates a flowchart of the operation of an electronic device according to various embodiments.
Figure 8:
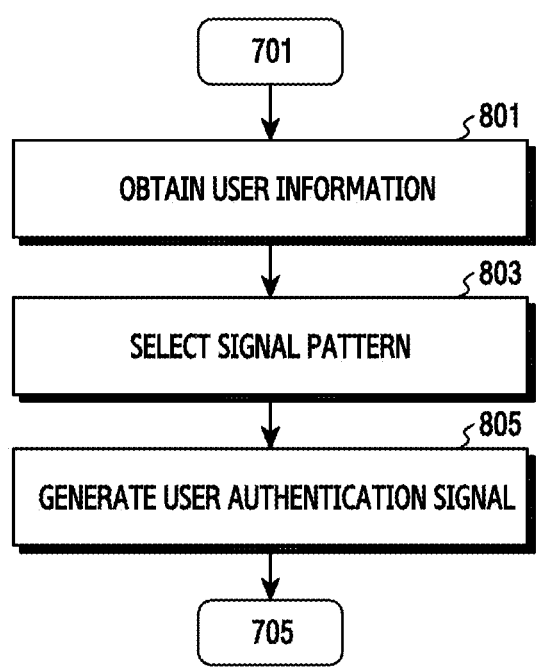
FIG. 8 illustrates a flowchart of a method of generating a user authentication signal of an electronic device according to various embodiments.

The operation of the first electronic device 400 is described in detail hereafter with reference to FIGS. 7 and 8. The first electronic device 400 may be the electronic device shown in FIGS. 1 and 2.

FIG. 7 illustrates a flowchart of the operation of an electronic device according to various embodiments.

Referring to FIG. 7, in operation 701, the electronic device 400 (for example, the processor 410) according to various embodiments can perform user authentication. The processor 410 can measure biometric information for the user authentication. The processor 410 (for example, the biometric module 411) can apply a measurement signal to a body through the electrode interface 450 by controlling the electrode interface 450. The measurement signal may be to apply a fine current to the body of a user. The processor 410 can selectively use the electrode interface 450, depending on measurement signals. The processor 410 can apply different measurement signals, depending on biometric information to be measured. The processor 410 can receive the applied measurement signal through a receiver of the electrode interface 450. For example, the processor 410 can obtain a voltage value (or a current value) from the measurement signal received through the receiver of the electrode interface 450. The processor 410 can obtain biometric information using the obtained voltage value (or current value). The biometric information may include at least one of heartbeat information, oxygen saturation information, body fat information, and stress information.

The processor 410 (for example, the biometric module 411) according to various embodiments can obtain biometric information using the sensor 460. For example, the processor 410 (for example, the user authentication module 413) can compare the obtained biometric information with biometric information stored in the memory 440. The processor 410 can determine whether the user of the biometric information is an authenticated user on the basis of the comparing result. For example, when the obtained biometric information is the same as the biometric information stored in the memory 440, the processor 410 can authenticate (or prove) that the obtained biometric information was measured from the user of the electronic device 400. However, when the obtained biometric information is not the same as the stored biometric information, the processor 410 can authenticate that the obtained biometric information was not measured from the user of the electronic device 400.

According to various embodiments, when the measured biometric information is not the same as the stored biometric information, the processor 410 may request measuring of biometric information again. The processor 410 may again perform user authentication by comparing biometric information measured by the request with the stored biometric information. For example, when user authentication fails (for example, the measured biometric information is not the same as the stored biometric information) even once, the processor 410 can end user authentication. Alternatively, the processor 410 can again perform user authentication over a predetermined number of times (for example, three times). The processor 410 can count 1 as the number of times of user authentication every time user authentication is failed. The processor 410 can end user authentication when the number of times of user authentication is a predetermined number of times or more.

The processor 410 (for example, the user authentication module 413) according to various embodiments may perform user authentication using a password or a lock pattern. For example, when a password input through a keypad is the same as a password stored in the memory 440, the processor 410 can complete user authentication.

In operation 703, the electronic device 400 (for example, the processor 410) according to various embodiments can generate a user authentication signal. When user authentication is completed, the processor 410 (for example, the signal generation module 415) can select at least one signal pattern on the basis of user information and generate a specific current for user authentication at a specific wavelength band as a user authentication signal by using the selected signal pattern. The processor 410 can change the frequency using device information of the electronic device 400 or can generate the specific current by processing the selected signal pattern. The device information can include at least one of time information, position information, and sequence information.

The electronic device 400 (for example, the processor 410) according to various embodiments can determine whether a second electronic device (for example, the second electronic device 500) is sensed. For example, the second electronic device 500 may be a device (or a sensor) that can measure biometric information of a user. For example, the measurement signal is to apply a current to the body of a user, and when noise is included in a measurement signal measured by the applied current, the processor 410 can determine that the second electronic device 500 is in contact with the body of the user. Alternatively, the processor 410 can sense the second electronic device 500 on the basis of user input. Alternatively, when the second electronic device 500 exists within a distance (for example, 10 cm, 30 cm, and 1 m) adjacent to the electronic device 400, the processor 410 can sense the second electronic device 500.

The processor 410 according to various embodiments can generate the user authentication signal before, simultaneously with, or after detecting the second electronic device 500.

In operation 705, the electronic device 400 (for example, the processor 410) according to various embodiments can apply the generated user authentication signal or a signal including at least a portion of the user authentication signal to the electrode interface 450. Since the electronic device 400 and the second electronic device 500 are in contact with the body of a user, when a current corresponding to the user authentication signal is applied to the electrode interface 450 being in contact with the body of the user, the second electronic device 500 can receive the applied current. Since the second electronic device 500 also applies a current to the body of the user to measure biometric information of the user, the second electronic device 500 can receive the user authentication signal together with a measurement signal received by the current applied through the body of the user. The processor 410 (for example, the control module 417) can apply the entire or a portion of the user authentication signal to the electrode interface 450. The processor 410 (for example, the control module 417) according to various embodiments can apply the user authentication signal to the electrode interface 450 together with other signals (for example, a control signal, a detection signal, and a measurement signal).

In operation 707, the electronic device 400 (for example, the processor 410) according to various embodiments can store the biometric information and the user authentication signal in the memory 440. The processor 410 (for example, the control module 417) may separately store the biometric information and the user authentication signal or may combine and store the biometric information and the user authentication signal in the memory 440.

FIG. 8 illustrates a flowchart of a method of generating a user authentication signal of an electronic device according to various embodiments. FIG. 8 may be a flowchart showing in detail the operation 703 of FIG. 7.

Referring to FIG. 8, in operation 801, the electronic device 400 (for example, the processor 410) according to various embodiments can obtain user information. The user information may include at least one of the user accountant of the electronic device 400, the phone number of the electronic device 400, and information about the user (for example, name, age, height, and weight). The processor 410 (for example, the signal generation module 415) can extract user information stored in the memory 440. Alternatively, the processor 410 can obtain information about the user by analyzing the user account. Alternatively, the processor 410 can obtain information about the user by on the basis of use's history.

In operation 803, the electronic device 400 (for example, the processor 410) according to various embodiments can select a signal pattern on the basis of the user information. The signal pattern may have different patterns for each user or may be changed in accordance with the device information of the electronic device 400. The device information can include at least one of time information, position information, and sequence information. For example, the processor 410 (for example, the signal generation module 415) can select one signal pattern (for example, the fifth signal pattern) from a plurality of signal patterns (for example, 1~100) on the basis of the user information. Alternatively, the processor 410 can change the frequency of a signal pattern using the device information of the electronic device 400. Alternatively, the processor 410 can transmit the user information to a server (for example, a biometric authentication server or a medical institution server) and can receive a signal pattern corresponding to the user information from the server.

In operation 805, the electronic device 400 (for example, the processor 410) according to various embodiments can generate a user authentication signal. The processor 410 (for example, the signal generation module 415) can generate a specific current for user authentication as a user authentication signal at a specific frequency band using the selected signal pattern.

Figure 9:
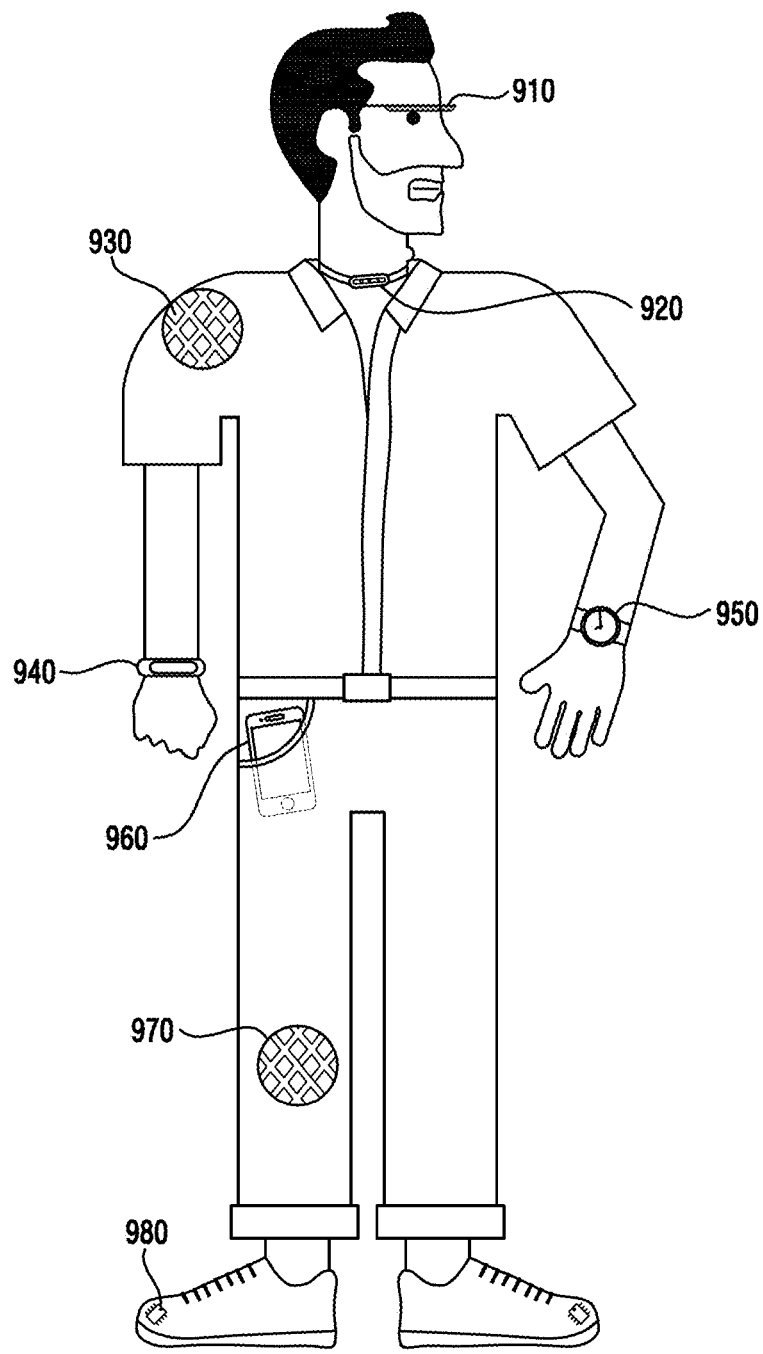
FIG. 9 illustrates a diagram of an example of a measuring sensor being in contact with the body of a user according to various embodiments.

FIG. 9 illustrates a diagram of an example of a measuring sensor being in contact with the body of a user according to various embodiments.

Referring to FIG. 9, the first electronic device 400 or the second electronic device 500 according to various embodiments can be brought in contact with the body. For example, the first electronic device 400 may include a wearable device 950 or a smartphone 960. The second electronic device 500 may include at least one of a glass sensor 910, a necklace sensor 920, a first clothing sensor 930, a bracelet sensor 940, a second clothing sensor 970, and a shoe sensor 980. For example, the glass sensor 910 can recognize user's gaze, iris, etc. as biometric information. The necklace sensor 920 can recognize user's breathing, oxygen saturation, heartbeat etc. as biometric information. The first clothing sensor 930 and second clothing sensor 970, which are fibers made of conductive threads, can recognize the resistance, temperature etc. of the body as biometric information. The bracelet sensor 940 can recognize oxygen saturation, heartbeat etc. as biometric information. The shoe sensor 980 can recognize walking, running, an exercise-distance, a consumed calorie etc. as a biometric information. The second electronic device 500 may include a processor (for example, an MCU) for electrode or sensor control. The first electronic device 400 or the second electronic device 500 can perform the operations of FIG. 6.

Figure 10:
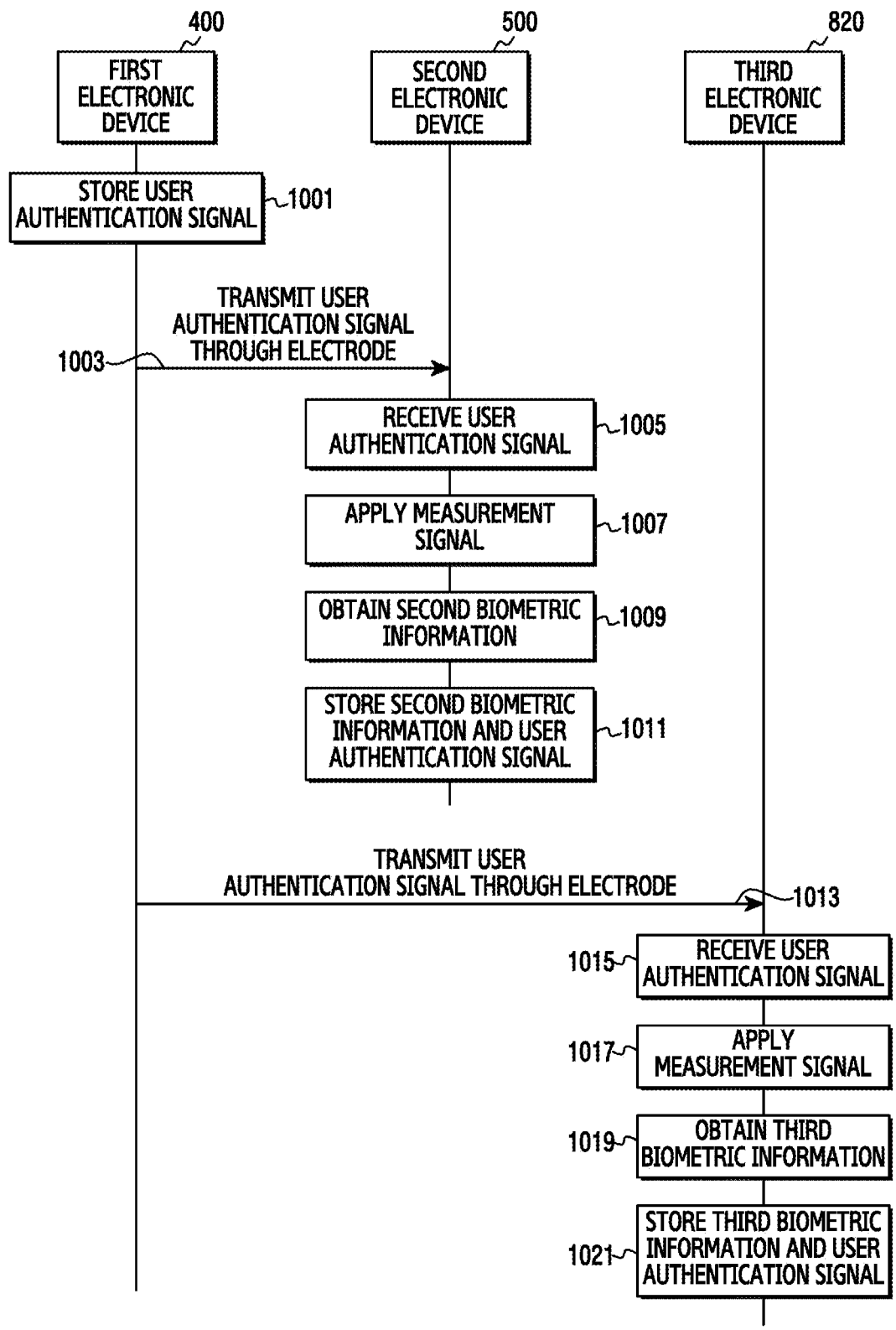
FIG. 10 illustrates a diagram of a method of obtaining user authentication-biometric information of a measuring sensor using an electronic device according to various embodiments.

FIG. 10 illustrates a case when a user has a health examination, in which the operations may be performed when a user has an examination through a plurality of biometric devices (for example, the second electronic device 500) with the first electronic device 400 on.

FIG. 10 illustrates a diagram showing a method of obtaining user authentication-biometric information of a measuring sensor using an electronic device according to various embodiments.

Referring to FIG. 10, in operation 1001, the first electronic device 400 according to various embodiments can store a user authentication signal. The user authentication signal can be generated using user information of the first electronic device 400. The first electronic device 400 can measure biometric information, but may be used to store the user authentication signal in a memory (for example, the memory 440) and transmit the user authentication signal when another electronic device (for example, the second electronic device) is detected. In FIG. 10, the first electronic device 400 may perform a function of transmitting the user authentication signal to another electronic device (for example, the second electronic device) without measuring biometric information. However, the first electronic device 400 may include an electrode interface to transmit the user authentication signal.

The first electronic device 400 according to various embodiments can operate in various ways, for example, applying a user authentication signal when user authentication is completed or periodically applying a user authentication signal. Alternatively, the first electronic device 400 can apply a user authentication signal when the second electronic device 500 is detected. For example, the first electronic device 400 can apply a detection signal to an electrode interface (for example, the electrode interface 450) periodically or in real time and can determine whether noise is included in a signal received by the detection signal. When noise is included in the received signal, the first electronic device 400 can determine that the second electronic device 500 is in contact with the body of a user. Alternatively, the first electronic device 400 can sense the second electronic device 500 on the basis of user input. Alternatively, when the second electronic device 500 exists within a distance (for example, 10 cm, 30 cm, and 1 m) adjacent to the first electronic device 400, the first electronic device 400 can sense the second electronic device 500. The first electronic device 400 according to various embodiments can apply the entire or a portion of the user authentication signal to the electrode interface 450 together with the detection signal.

In operation 1003, the first electronic device 400 according to various embodiments can apply a user authentication signal or a signal including at least a portion of a user authentication signal to an electrode interface (for example, the electrode interface 450). For example, when the user authentication signal is applied to the body of a user through the electrode interface 450, the user authentication signal can be transmitted to the second electronic device 500 through the body of the user. The electrode interface 450 can apply a current for the user authentication signal to the body of the user.

In operation 1005, the second electronic device 500 according to various embodiments can receive the user authentication signal. For example, the second electronic device 500 can receive a current for the user authentication signal from an electrode that is used for measuring biometric information.

In operation 1007, the second electronic device 500 according to various embodiments can apply a measurement signal (for example, the second measurement signal) to the body to measure biometric information. The second electronic device 500 may be a device (or a sensor) that can obtain only one item of biometric information or one or more items of biometric information related to the body. The second electronic device 500 can apply a current for the measurement signal to the body of the user through an electrode.

In operation 1009, the second electronic device 500 according to various embodiments can obtain second biometric information using the applied measurement signal. For example, the second electronic device 500 can obtain the second biometric information using a voltage value measured from the current applied to the body of the user or a resistance value of the body. Different measurement signals may be received, depending on biometric information to be measured. The second electronic device 500 can obtain second biometric information for a predetermined time by repeatedly performing the operations 1007 to 1009.

In operation 1011, the second electronic device 500 according to various embodiments can store the obtained second biometric information in a memory together with the user authentication signal. The second electronic device 500 can store the obtained second biometric information in connection with the user authentication signal. The second electronic device 500 can store the second biometric information in connection with the entire or a portion of the user authentication signal.

The first electronic device 400 according to various embodiments can apply a detection signal to an electrode interface (for example, the electrode interface 450) periodically or in real time and can determine whether noise is included in a signal received by the detection signal. When noise is included in the received signal, the first electronic device 400 can determine that a third electronic device 820 is in contact with the body of a user. The first electronic device 400 according to various embodiments can determine that the third electronic device 820 is a biometric device different from the second electronic device 500 on the basis of the noise included in the received signal or the distance from the third electronic device 820.

In operation 1013, the first electronic device 400 according to various embodiments can apply a user authentication signal or a signal including at least a portion of a user authentication signal to an electrode interface (for example, the electrode interface 450). For example, when the user authentication signal is applied to the body of a user through the electrode interface 450, the user authentication signal can be transmitted to the third electronic device 820 through the body of the user.

In operation 1013 according to various embodiments, when the second electronic device 500 is in contact with the body of the user, the user authentication signal can be transmitted to the second electronic device 500 and the third electronic device 820 through the body of the user.

In operation 1015, the third electronic device 820 according to various embodiments can receive the user authentication signal or a signal including at least a portion of the user authentication signal. For example, the third electronic device 820 can receive a current for the user authentication signal from an electrode that is used for measuring biometric information.

In operation 1017, the third electronic device 820 according to various embodiments can apply a measurement signal (for example, a third measurement signal) to measure biometric information. The third electronic device 820 may be a device (or a sensor) that can obtain only one item of biometric information or one or more items of biometric information related to the body. The third electronic device 820 can apply a current for the measurement signal to the body of the user through an electrode.

In operation 1019, the third electronic device 820 according to various embodiments can obtain third biometric information using a signal received by the applied measurement signal. For example, the third electronic device 820 can obtain the third biometric information using a voltage value measured from the current applied to the body of the user or a resistance value of the body. The third electronic device 820 can obtain third biometric information for a predetermined time by repeatedly performing the operations 1017 to 1019.

In operation 1021, the third electronic device 820 according to various embodiments can store the obtained third biometric information in a memory together with the user authentication signal. The third electronic device 820 can store the obtained third biometric information in connection with the user authentication signal. The third electronic device 820 can store the third biometric information in connection with the entire or a portion of the user authentication signal.

Figure 11:
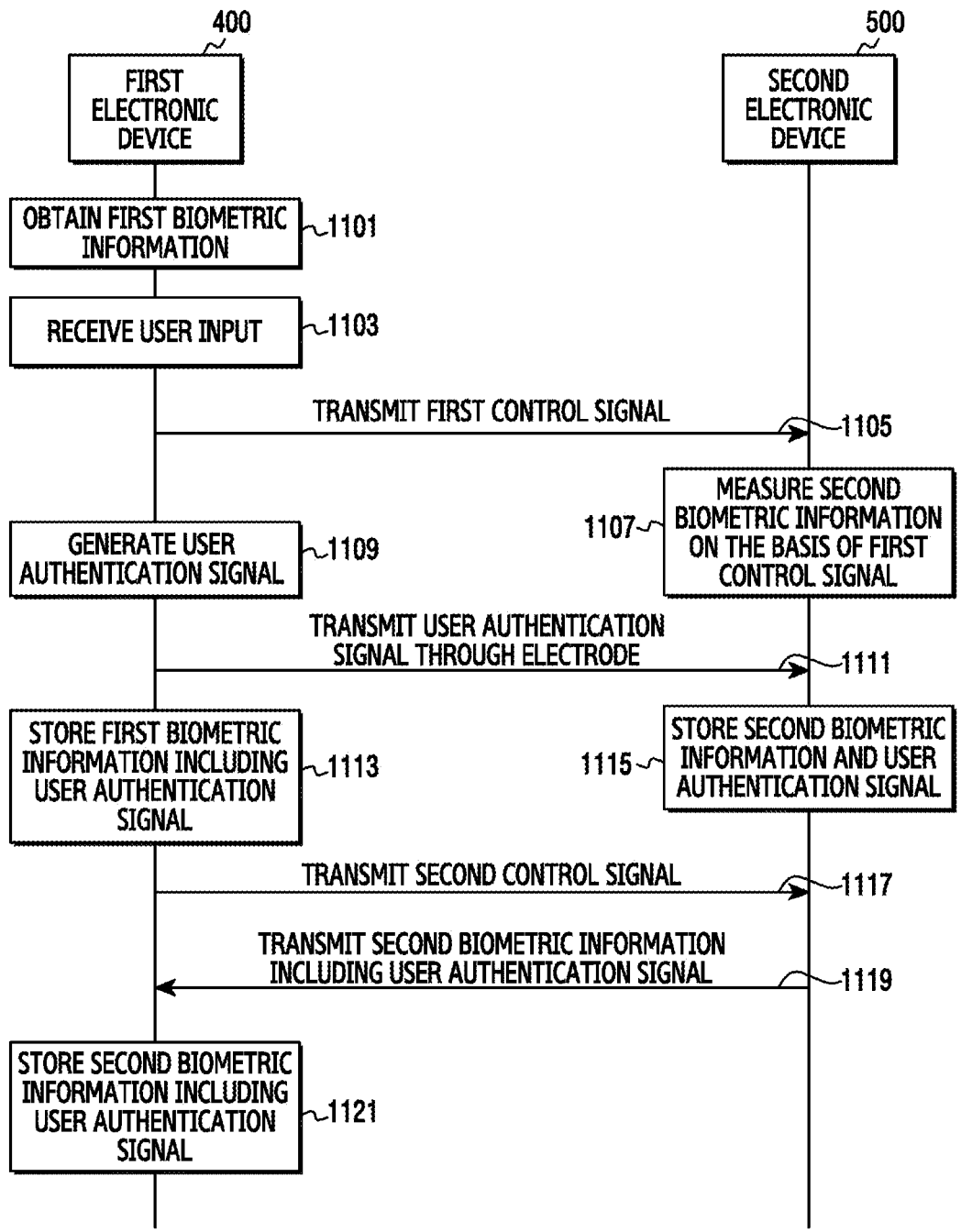
FIG. 11 illustrates a flowchart of a method of obtaining user authentication-biometric information of an electronic device according to various embodiments.

FIG. 11 illustrates a flowchart showing a method of obtaining user authentication-biometric information of an electronic device according to various embodiments.

Referring to FIG. 11, in operation 1101, the first electronic device 400 according to various embodiments can obtain first biometric information. The first electronic device 400 can apply a first measurement signal for measuring biometric information to an electrode interface (for example, the electrode interface 450) and can obtain the first biometric information using a value received by the applied first biometric information. The operation 1101 can be continuously repeatedly performed even while the operation 1103, 1109, 1113 or 1121 is performed.

In operation 1103, the first electronic device 400 according to various embodiments can receive user input. The user input may be input for applying a control signal. The control signal may be a signal for controlling another electronic device (for example, the second electronic device 500). The control signal may include at least one of a control signal for turning on/off the second electronic device 500, a control signal for instruction (or order) to measure specific biometric information, and a control signal for instruction to transmit biometric information (for example, the second biometric information) measured by the second electronic device 500. The control signal according to various embodiments can be transmitted to the second electronic device 500 through the body of the user, wire communication, or wireless communication. For example, when it is sensed that the second electronic device 500 is brought in contact with the body of a user, the first electronic device 400 can display whether the second electronic device 500 is detected on a user interface displayed on the display 420. The user can select a control signal to transmit to the second electronic device 500 through the user interface displayed on the display 420.

In operation 1105, the first electronic device 400 according to various embodiments can transmit a first control signal. The first electronic device 400 can apply the first control signal through the body of the user by applying a current corresponding to the first control signal to an electrode interface (for example, the electrode interface 450). The first control signal may be an instruction to measure specific biometric information. The first electronic device 400 according to various embodiments can transmit the first control signal together with the entire or a portion of a user authentication signal through the body of the user.

In operation 1107, the second electronic device 500 according to various embodiments can measure second biometric information on the basis of the first control signal. For example, the second electronic device 500 may be a device that can measure one or more items of biometric information. The second electronic device 500 may be a device that can measure at least two of items of biometric information including heartbeat information, oxygen saturation information, electromyogram information, electroencephalogram information, body fat information, and stress information. When the first control signal is an instruction to measure electroencephalogram information, the second electronic device 500 can measure electroencephalogram information as the second biometric information.

In operation 1109, the first electronic device 400 according to various embodiments can generate a user authentication signal. For example, the first electronic device 400 can perform user authentication using the first biometric information, and can generate the user authentication signal on the basis of user information when the user authentication is completed.

In operation 1111, the first electronic device 400 according to various embodiments can transmit a user authentication signal or a signal including at least a portion of a user authentication signal through an electrode interface (for example, the electrode interface 450). The first electronic device 400 can transmit the user authentication signal to the second electronic device 500 by applying a current corresponding to the user authentication signal to the electrode interface 450.

Although operations 1105 and 1111 are separately performed in the above description, operations 1105 and 1111 may be simultaneously performed. In this case, the first electronic device 400 can obtain first biometric information, generate a user authentication signal, and transmit a first control signal and the user authentication signal when receiving user input. Alternatively, the user authentication signal may be included in the first control signal. The first electronic device 400 according to various embodiments can store the user authentication signal in the memory 440, and can transmit the first control signal and the user authentication signal without user input when user authentication using the first biometric signal is completed.

In operation 1113, the first electronic device 400 according to various embodiments can store first biometric information including (for example, the entire or a portion of) the user authentication signal in a memory (for example, the memory 440).

In operation 1115, the second electronic device 500 according to various embodiments can store second biometric information including (for example, the entire or a portion of) the user authentication signal in a memory.

Operations 1113 and 1115 may be performed simultaneously, separately, or sequentially.

In operation 1117, the first electronic device 400 according to various embodiments can transmit a second control signal. The first electronic device 400 may apply a current corresponding to the second control signal to an electrode interface (for example, the electrode interface 450). The second control signal may be an instruction to transmit biometric information (for example, the second biometric information) measured by the second electronic device 500. The first electronic device 400 according to various embodiments can transmit the second control signal to the second electronic device 500 through wire communication or wireless communication. When the first electronic device 400 is connected with the second electronic device 500 through an interface (for example, the interface 270), the first electronic device 400 can transmit the second control signal to the second electronic device 500 through the interface. Alternatively, when the first electronic device 400 is connected with the second electronic device 500 through near field communication (for example, Bluetooth), the first electronic device 400 can transmit the second control signal to the second electronic device 500 through near field communication.

In operation 1119, the second electronic device 500 according to various embodiments can transmit second biometric information including a user authentication signal in response to the second control signal. For example, the second electronic device 500 can receive the second control signal through the body of the user. Alternatively, the second electronic device 500 can receive the second control signal from the first electronic device 400 through wire communication or wireless communication. The second electronic device 500 can separately transmit the second biometric information and the user authentication signal or can transmit one signal combining the second biometric information and the user authentication signal.

In operation 1121, the first electronic device 400 according to various embodiments can store second biometric information including a user authentication signal in a memory (for example, the memory 440). The first electronic device 400 can receive the second biometric information including the user authentication signal from the second electronic device 500 and can store the received second biometric information including the user authentication signal in a memory (for example, the memory 440). The first electronic device 400 according to various embodiments can determine whether the user authentication signal is included in the second biometric information or whether the user authentication signal has been received together with the second biometric information. When the user authentication signal is included in the second biometric information or the user authentication signal has been received together with the second biometric information, the first electronic device 400 can store the second biometric information in the memory 440.

Figure 12:
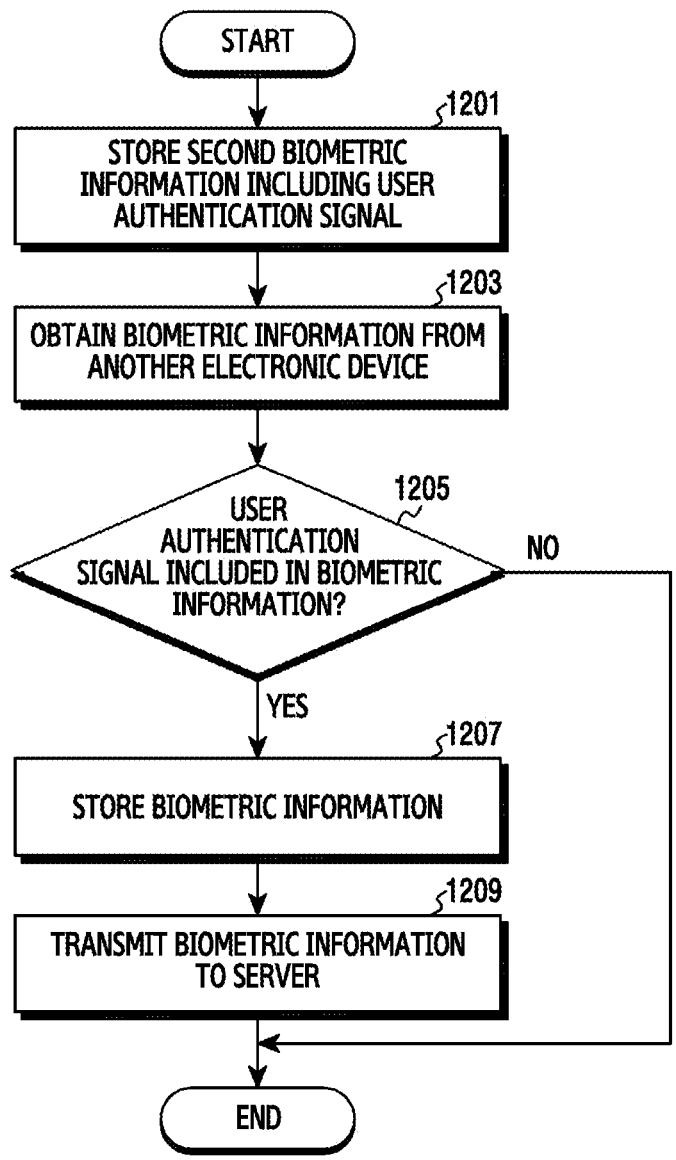
FIG. 12 illustrates a flowchart of a method of obtaining user authentication-biometric information of an electronic device according to various embodiments.

FIG. 12 illustrates a flowchart showing a method of obtaining user authentication-biometric information of an electronic device according to various embodiments.

Referring to FIG. 12, in operation 1201, the first electronic device 400 (for example, the processor 410) according to various embodiments can be connected with another electronic device. For example, the processor 410 can apply a detection signal to an electrode interface (for example, the electrode interface 450) periodically or in real time and can determine whether noise is included in a signal received by the detection signal. When noise is included in the received signal, the processor 410 can determine that another electronic device (for example, the second electronic device 500) is in contact with the body of a user. When the second electronic device 500 is brought in contact with the body of a user, the processor 410 can be connected with the second electronic device 500. Alternatively, the processor 410 can be connected with the second electronic device 500 through wire communication or wireless communication. The processor 410 can be connected with the second electronic device 500 through an interface (for example, the interface 270) or near field communication (for example, Bluetooth).

In operation 1203, the first electronic device 400 (for example, the processor 410) according to various embodiments can obtain biometric information (for example, second biometric information) from another electronic device (for example, the second electronic device 500). The processor 410 can obtain the biometric information through the body of a user. The biometric information may be measured by the second electronic device 500. Alternatively, the processor 410 can receive the biometric information from the second electronic device 500 through wire communication or wireless communication.

In operation 1205, the first electronic device 400 (for example, the processor 410) according to various embodiments can determine whether a user authentication signal is included in the biometric information. The processor 410 can determine whether the entire or a portion of the user authentication signal is included in the biometric information. Another electronic device (for example, the second electronic device 500) can separately transmit the biometric information and the user authentication signal or can transmit one signal combining the biometric information and the user authentication signal.

The processor 410 can perform operation 1207 when a user authentication signal is included in the biometric information and can end the operation when a user authentication signal is not included in the biometric information.

The first electronic device 400 (for example, the processor 410) according to various embodiments can request re-measuring of biometric information when a user authentication signal is not included in the biometric information. When requesting re-measuring, the processor 410 can transmit a user authentication signal stored in a memory (for example, the memory 440) to the other electronic device (for example, the second electronic device 500).

In operation 1207, the first electronic device 400 (for example, the processor 410) according to various embodiments can temporarily store biometric information in a memory (for example, the memory 440). When (the entire or a portion of) the user authentication signal is included in the biometric information or the user authentication signal has been received together with the biometric information, the processor 410 can store the biometric information in the memory 440.

In operation 1209, the first electronic device 400 (for example, the processor 410) according to various embodiments can transmit the biometric information to a server. For example, the processor 410 can transmit biometric information stored in the memory 440 in real time, periodically, or in response to a request from a server.

A computer-readable recording medium according to various embodiments may include programs for performing an operation of obtaining user information by performing user authentication, an operation of generating a user authentication signal on the basis of the user information, and an operation of transmitting the user authentication signal or a signal including at least a portion of the user authentication signal through the body of a user being in contact with an electrode interface.

A computer-readable recording medium according to various embodiments may include programs for performing an operation of obtaining at least one item of biometric information using an electrode interface, an operation of receiving a user authentication signal or a signal including at least a portion of the user authentication signal from the electrode interface, and an operation of storing the at least one biometric information in a memory together with the user authentication signal.

The computer-readable recording medium may include a hard disk, floppy disk, a magnetic medium (for example, a magnetic tape), an optical recording medium (for example, a CD-ROM and a DVD), a magnet-optical medium (for example, a floptical disk), and an internal memory. Commands may include codes constructed by a compiler or codes that can be executed by an interpreter. Modules or program modules according to various embodiments may include at least one or more of the components described above, may be partially omitted, or may further include other components. Operations that are performed by modules, program modules, or other components according to various embodiments may be performed sequentially, in parallel, repeatedly, or heuristically, or at least some operation may be performed in another order or omitted, or other operations may be added.

Further, the embodiments described and shown in the specification and the drawings are specific examples for easily explaining the present disclosure and helping understand the present disclosure, and do not limit the scope of the present disclosure. Therefore, other than the embodiments described herein, all of changes or modifications based on the spirit of the present disclosure should be construed as being included in the scope of the present disclosure.

Although the present disclosure has been described with an exemplary embodiment, various changes and modifications may be suggested to one skilled in the art. It is intended that the present disclosure encompass such changes and modifications as fall within the scope of the appended claims.

What is claimed is:
1. An electronic device comprising:
an electrode interface comprising one or more electrodes and configured to transmit and receive electrical signals via the one or more electrodes, through a body of a user;
a memory; and
a processor operably coupled to the electrode interface and the memory, the processor configured to:
obtain first biometric information;
authenticate the user based on the first biometric information;
generate a user authentication signal based on user information, wherein the user information is stored in the memory and includes at least one of a user's account, phone number, or information related to the user;
transmit, via the electrode interface, a first signal comprising at least a portion of the user authentication signal and a control signal for obtaining second biometric information to a second electronic device attached to the body of the user;
receive, via the electrode interface, a second signal comprising the second biometric information and the at least a portion of the user authentication signal, wherein the second signal is transmitted from the second electronic device; and
store, the second biometric information and the at least a portion of the user authentication signal in the memory.

2. The electronic device of claim 1, further comprising:
a sensor separated from the electrode interface, wherein the sensor is configured to obtain biometric information,
wherein the processor is further configured to:
authenticate the user based on the first biometric information obtained from at least one of the sensor and the electrode interface.

3. The electronic device of claim 2, wherein the processor is further configured to:
authenticate the user based in part on a comparison between the first biometric information obtained from at least one of the sensor and the electrode interface and reference biometric information stored in the memory.

4. The electronic device of claim 3, wherein the user is authenticated when the first biometric information obtained from the at least one of the sensor and the electrode interface is identical to the reference biometric information.

5. The electronic device of claim 1, wherein the processor is further configured to:
select a signal pattern based on the user information; and
generate, using the signal pattern, a designated current for a user authentication on a designated frequency band as the user authentication signal.

6. The electronic device of claim 5, wherein the signal pattern is changed according to device information of the electronic device.

7. The electronic device of claim 6, wherein the device information includes at least one of time information, location information, or sequence information, and wherein the processor is further configured to change, using the device information, the signal pattern.

8. The electronic device of claim 1, wherein the processor is further configured to transmit, to the second electronic device attached to the body of the user, at least the portion of the user authentication signal.

9. The electronic device of claim 1, wherein the processor is further configured to store, in the memory, the user information associated with the user authentication signal.

10. The electronic device of claim 1, further comprising: a communication interface,
wherein the processor is further configured to receive, through the communication interface, the second biometric information measured by the second electronic device.

11. The electronic device of claim 10, wherein the processor is further configured to:
determine whether the user authentication signal is included in the second biometric information; and
when the processor determines that the user authentication signal is included in the second biometric information, store the received second biometric information in the memory.

12. An electronic device attachable to a body of a user, the electronic device comprising:
an electrode interface comprising one or more electrodes and configured to transmit and receive electrical signals via the one or more electrodes, through the body of the user;
a memory; and
a processor operably coupled to the electrode interface and the memory, the processor configured to:
receive, via the electrode interface, a first signal comprising at least a portion of a user authentication signal and a control signal for obtaining biometric information, wherein the first signal is transmitted from a second electronic device;
obtain, in response to receiving the first signal, biometric information of the user from the electrical signals obtained from the body of the user via the electrode interface; and
transmit, via the electrode interface, a second signal comprising the biometric information and the at least a portion of the user authentication signal to the second electronic device.

13. The electronic device of claim 12, wherein the processor is further configured to:
receive the control signal from the electrode interface; and
apply, based on the control signal, a measurement signal for obtaining the biometric information to the electrode interface.

14. The electronic device of claim 12, further comprising: a communication interface,
wherein the processor is further configured to:
when the processor receives a transmission control signal from the communication interface, provide, through the communication interface, the biometric information including the user authentication signal to the second electronic device.

15. A system comprising:
a first electronic device, including:
a first electrode interface comprising one or more electrodes, and configured to transmit and receive signals via the one or more electrodes, through a body of a user; and
a first processor operably coupled to the first electrode interface, wherein the first processor is configured to:
obtain first biometric information;
authenticate the user based on the first biometric information;
generate a user authentication signal based on user information, wherein the user information is stored in a memory and includes at least one of a user's account, phone number, or information related to the user; and
transmit, via the first electrode interface, a first signal comprising at least a portion of the body of the user authentication signal and a control signal for obtaining second biometric information to a second electronic device attached the body of the user,
the second electronic device, including:
a second electrode interface comprising one or more electrodes and configured to transmit and receive electrical signals via the one or more electrodes, through the body of the user; and
a memory; and
a second processor, operably coupled to the second electrode interface and the memory, wherein the second processor is configured to:
receive, via the second electrode interface, the first signal comprising the at least a portion of the body of the user authentication signal and the control signal for obtaining the second biometric information, wherein the first signal is transmitted from the first electronic device;
obtain, in response to receiving the first signal, the second biometric information of the user from the electrical signals obtained from the body of the user via the second electrode interface; and
transmit, via the second electrode interface, a second signal comprising the second biometric information and the at least a portion of the user authentication signal to the first electronic device.

16. The system of claim 15, wherein the first processor is further configured to:
obtain the first biometric information by using the at least one of the first electrode interface or a biometric recognition sensor;
authenticate the user based on the first biometric information; and
in response to authenticating the user, generate the user authentication signal.

17. The system of claim 15, wherein the first processor is further configured to:
select at least one signal pattern based on the user information; and
generate, by using the at least one signal pattern, a designated current for user authentication on a designated frequency band as the user authentication signal.

18. The system of claim 15, wherein the first processor is further configured to:
transmit, from the first electrode interface to the second electronic device, through the body of the user at least the portion of the user authentication signal.

19. The system of claim 15, wherein the first processor and the second processor are further configured to obtain identical biometric information or different biometric information.

20. The system of claim 15, wherein the first processor is further configured to:
apply a detection signal to the first electrode interface; and determine that the second electronic device is attached to at least another portion of the body of the user, if a noise is included in the detection signal.

\* \* \* \* \*